United States Patent
Hsu et al.

(10) Patent No.: US 11,737,351 B2
(45) Date of Patent: Aug. 22, 2023

(54) ORGANIC SEMICONDUCTOR MATERIAL AND ORGANIC PHOTOELECTRIC DEVICE USING THE SAME

(71) Applicant: Raynergy Tek Incorporation, Hsinchu (TW)

(72) Inventors: Chain-Shu Hsu, Hsinchu (TW); Jun-Yan Yu, Hsinchu (TW); You-Wei Lin, Hsinchu (TW); Kuan-Lin Peng, Hsinchu (TW); Yi-Ming Chang, Hsinchu (TW); Chuang-Yi Liao, Hsinchu (TW); Huei Shuan Tan, Hsinchu (TW)

(73) Assignee: RAYNERGY TEK INCORPORATION, Hsinchu (TW)

( * ) Notice: Subject to any disclaimer, the term of this patent is extended or adjusted under 35 U.S.C. 154(b) by 271 days.

(21) Appl. No.: 16/845,944

(22) Filed: Apr. 10, 2020

(65) Prior Publication Data
US 2020/0328361 A1    Oct. 15, 2020

Related U.S. Application Data

(60) Provisional application No. 62/833,065, filed on Apr. 12, 2019.

(51) Int. Cl.
*H10K 85/40*     (2023.01)
*C07F 7/08*      (2006.01)
(Continued)

(52) U.S. Cl.
CPC ........... *H10K 85/40* (2023.02); *C07D 495/14* (2013.01); *C07F 7/0816* (2013.01);
(Continued)

(58) Field of Classification Search
CPC ............. H01L 51/0094; H01L 51/4253; H01L 51/442; C07D 495/14; C07F 7/0816
See application file for complete search history.

(56) References Cited

U.S. PATENT DOCUMENTS

2012/0248878 A1* 10/2012 Iwanaga ................ B82Y 10/00
                                                              136/263

FOREIGN PATENT DOCUMENTS

| CN | 106543200 A | * | 3/2017 |
| CN | 106543200 A |   | 3/2017 |
| TW | 201900650 A |   | 1/2019 |

OTHER PUBLICATIONS

Guo et al., CN 106543200 A, English Machine Translation. (Year: 2017).*

(Continued)

*Primary Examiner* — Tae-Sik Kang
(74) *Attorney, Agent, or Firm* — WPAT, P.C

(57) ABSTRACT

Organic photoelectric device comprises a first electrode, a first carrier transfer layer, an active layer, a second carrier transfer layer and a second electrode. The first electrode is a transparent electrode. The active layer includes at least one organic semiconductor material including a structure such as Formula I:

(Formula I)

(Continued)

The second carrier transfer layer is composed between the active layer and the second electrode. When X1 and X2 are selected from one of Si, Ge and derivatives thereof, the active layer further includes an organic solvent, and the solubility of the organic solvent to the active layer is not less than 5 mg/mL. When X1 and X2 are selected from one of C and its derivatives, the active layer further includes an additive. The power conversion efficiency of the organic photoelectric device of the present invention can be up to more than 14%.

7 Claims, 8 Drawing Sheets

(51) Int. Cl.
  *C07D 495/14* (2006.01)
  *H10K 85/60* (2023.01)
  *H10K 30/30* (2023.01)
  *H10K 30/82* (2023.01)

(52) U.S. Cl.
  CPC .......... *H10K 85/657* (2023.02); *H10K 30/30* (2023.02); *H10K 30/82* (2023.02)

(56) References Cited

OTHER PUBLICATIONS

Lo et al., "Every Atom Counts: Elucidating the Fundamental Impact of Structural Change in Conjugated Polymers for Organic Photovoltaics", Chem. Mater. 2018, 30, 2995-3009. (Year: 2018).*
Taiwan Intellectual Property Office, office action dated Nov. 25, 2020.
Zhang et al. "Conjugated polymers based on C, Si and N-bridged dithiophene and thienopyrroledione units: synthesis, filed-effect transistors and bulk heterojunction polymer solar cells", Nov. 15, 2010, Journal of Materials Chemistry.

* cited by examiner

ORGANIC SEMICONDUCTOR MATERIAL AND ORGANIC PHOTOELECTRIC DEVICE USING THE SAME

The present application is based on, and claims priority from, America provisional patent application number U.S. 62/833,065, filed on 2019 Apr. 12, the disclosure of which is hereby incorporated by reference herein in its entirety.

BACKGROUND OF THE INVENTION

Field of the Invention

The present invention relates to an organic semiconductor material applied to an organic photoelectric device, and an organic photoelectric device including the said organic semiconductor material.

Description of the Prior Art

In view of global warming, climate change has become a common challenge in the international communities. The Kyoto protocol proposed by the "United Nations Framework Convention on Climate Change (UNFCCC)" in 1997 which had entered into force in 2005 is aimed at reducing carbon dioxide emissions. In this regard, countries are focusing on the development of renewable energy to reduce the use of petrochemical fuels. As the sun provides far enough energy needs of people at present and for the future, renewable energy becomes a major concern for solar power generation, which has led to the use of organic photoelectric devices for solar power generation as the primary development target.

Compared with the existing silicon-based organic photoelectric devices, the new type of organic photoelectric devices is not only cheap in production cost and light weight, but also can be thin, transparent and flexible as plastic films, so that the new type of organic photoelectric devices is suitable for making various shapes. The organic photoelectric devices can be widely used in communication, architecture, transportation, lighting, fashion and other fields. Therefore, the new generation of organic photoelectric devices not only contributes to environmental protection during global climate change, but also has great economic potential.

Organic photoelectric devices can utilize bulk heterojunction (BHJ) structures as devices with basic application characteristics. In a recent research report, the maximum power conversion efficiency (PCE) of BHJ organic photoelectric devices combining a low-bandgap conjugated polymer crystal with a fullerene derivative is 8%. The morphology of the active layer in such BHJ organic photoelectric devices plays a key role in the overall performance of the device. The phase separation region in the active layer can provide a way for the charge separation carriers of the interface photogenerated excitons to be transmitted to their corresponding electrodes, and must still have a relatively sufficient amount of heterojunction to provide excitons separation. By using thermal annealing, solvent annealing, or adding a solvent additive, the shape of the active layer can be improved to a more powerful state, and the performance of the organic photoelectric device is relatively improved. In the case of using additives, it may lead to the following situation: (1) the material of the active layer self-organizes into a polymer with an ordered structure; (2) the active layer has a suitable region for fullerene derivative aggregation regions to appropriately provide a charge carrier transport network.

However, the raw material cost of fullerene and its derivatives is more expensive, and it is difficult to prepare and purity. In addition, the absorption in the visible light region is low, and it is difficult to widen. Therefore, the development of organic semiconductor materials for non-fullerene polymers and small molecule materials has been started and widely used in organic photoelectric devices. Small molecule materials have a direct molecular structure and there is no difference in synthetic batches. Therefore, research on organic semiconductor materials with small organic molecules has also attracted widespread attention. In recent years, the power conversion efficiency of fullerene based small molecule organic photoelectric devices has been comparable to that of polymer organic photoelectric devices, but the performance of small molecule organic photoelectric devices made of non-fullerene organic semiconductor materials is poor, and the power conversion efficiency of small molecule organic photoelectric devices can achieve only 7%. Since the non-fullerene small molecule organic semiconductor materials have the dual advantages of non-fullerene organic semiconductor materials and small molecule organic semiconductor materials, how to provide a non-fullerene small molecule organic semiconductor material with high power conversion efficiency and an organic photoelectric device using the organic semiconductor material is a very important issue at present.

SUMMARY OF THE INVENTION

In view of this, one category of the present invention is to provide an organic semiconductor material to break through the power conversion efficiency of the prior art. According to a specific embodiment of the present invention, the organic semiconductor material comprises a structure of Formula I:

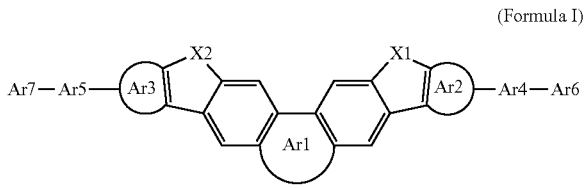

(Formula I)

Wherein, X1 and X2 can be the same or different, and X1 and X2 are independently selected from one of the following: C, Si, Ge and derivatives thereof; Ar1 is selected from the group consisting of five-member heterocyclic ring with and without substitutions, and six-member heterocyclic ring with and without substitutions; Ar2 and Ar3 can be the same or different, and Ar2 and Ar3 are independently selected from the group consisting of aromatic ring with and without substitutions, heterocyclic ring with and without substitutions, fused ring with and without substitutions and fused heterocyclic ring with and without substitutions, wherein Ar2 and Ar3 include at least one of five-member ring and six-member ring, and the number of the rings is 1 to 3; Ar4 and Ar5 can be the same or different, and Ar4 and Ar5 are independently selected from the group consisting of aromatic ring with and without substitutions, heterocyclic ring with and without substitutions, fused ring with and without substitutions and fused heterocyclic ring with and without substitutions, wherein Ar4 and Ar5 include at least one of five-member ring and six-member ring, and the number of the rings is 0 to 3; Ar6 and Ar7 can be the same or different, and Ar6 and Ar7 are independently selected from the group consisting of electron-withdrawing aromatic ring with and without substitutions, electron-withdrawing heterocyclic ring with and without substitutions, electron-withdrawing fused ring with and without substitutions and electron-withdrawing fused heterocyclic ring with and without substitutions; Ar6 bonds to Ar2 or Ar4 with sing bond or double bond; and Ar7 bonds to Ar3 or Ar5 with sing bond or double bond.

Wherein, the substitution of the formula I is selected from the group consisting of: C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

In one embodiment, Ar1 comprises the structure of formula II:

(Formula II)

Wherein, X3 is selected from one of following: C, S, Se, Te, NR1, CR1$_2$ and SiR1$_2$, and R1 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

In one embodiment, Ar1 comprising the structure of formula III:

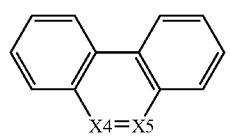

(Formula III)

Wherein, X4 and X5 can be the same or different, and X4 and X5 are independently selected from the following: C, N, CR2 and NR2, and R2 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, Ct-C30 nitro-containing carbon chain, C1-C30 hydroxy-containing carbon chain. C1-C30 keto-containing carbon chain, oxygen and halogen.

In one embodiment, Ar2 and Ar3 are independently selected from the following structure:

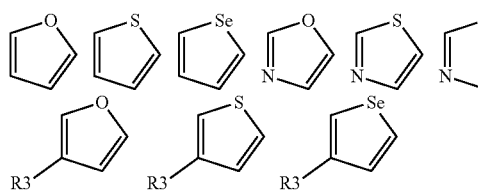

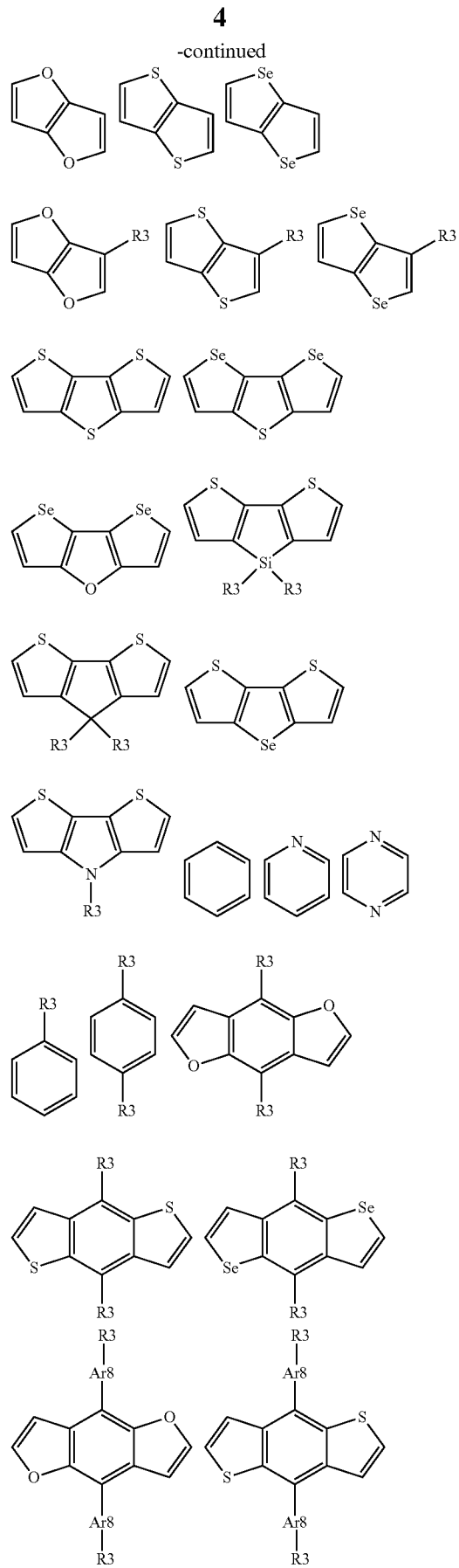

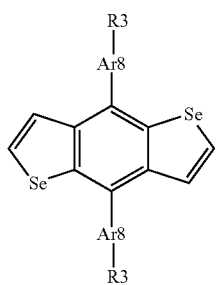

Wherein, R3 is selected from the group consisting of C1-C30 alkyl, C1-C30 branched alkyl, C1-C30 silyl, C1-C30 ester. C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen; and Ar8 is selected from the group consisting of aromatic ring with and without substitutions, heterocyclic ring with and without substitutions, fused ring with and without substitutions and fused heterocyclic ring with and without substitutions.

In one embodiment, Ar4 and Ar5 are independently selected from the following structure:

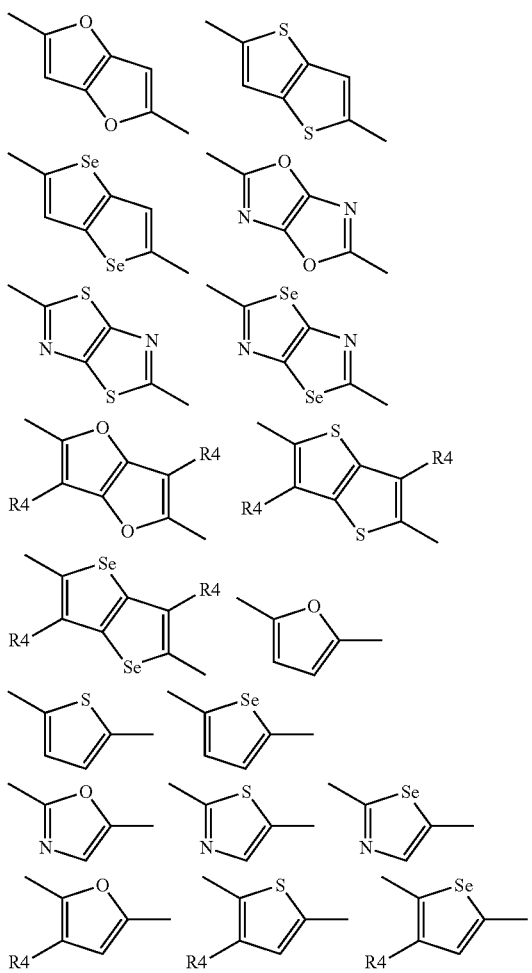

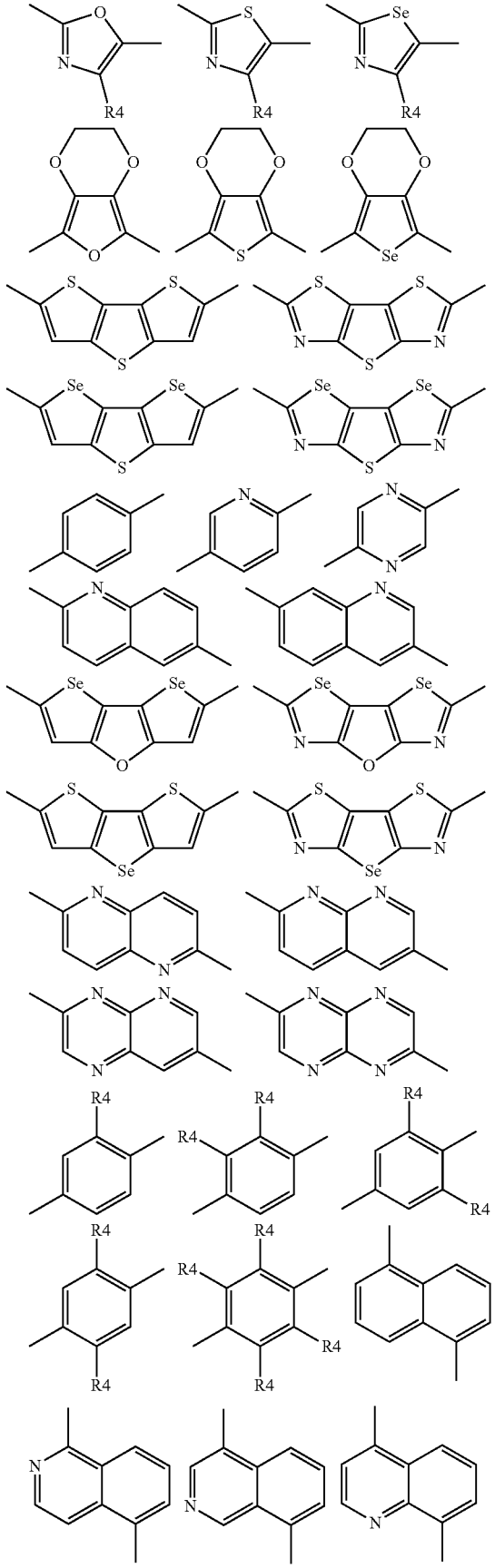

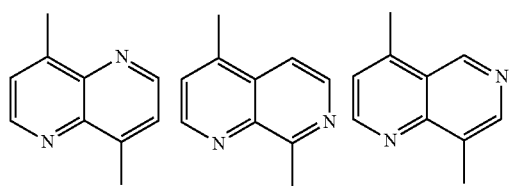

wherein, R4 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

In one embodiment, Ar6 and Ar7 are independently selected from the following structure:

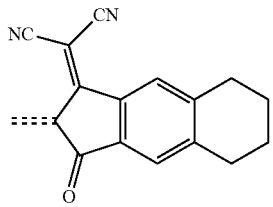

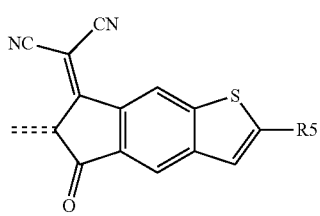

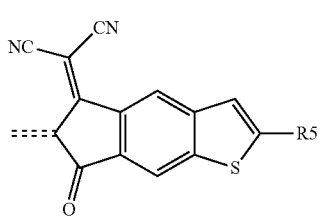

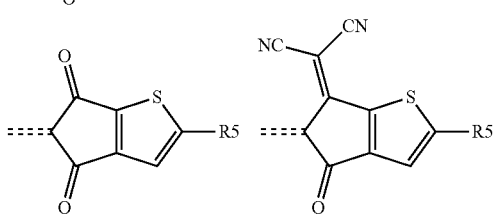

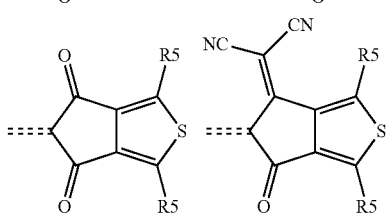

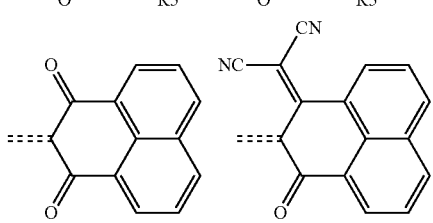

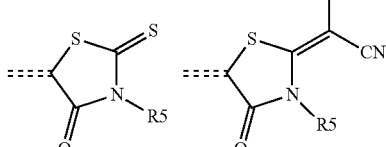

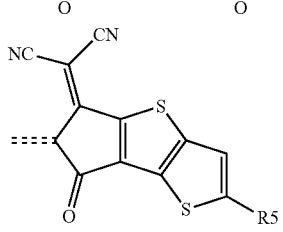

-continued

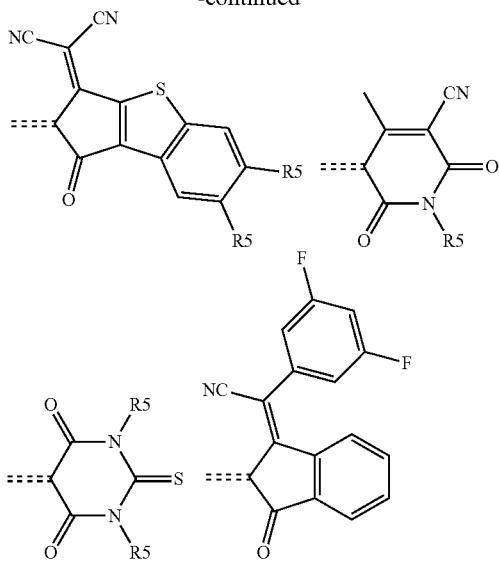

wherein, R5 is selected from the group consisting of C1-C20 alkyl, C1-C20 alkoxy, C1-C20 carbonyl, C1-C20 ester, cyano, oxygen, hydrogen, and halogen.

Another category of the present invention is to provide an organic photoelectric device comprises a first electrode including a transparent electrode, a first carrier transfer layer, an active layer which at least comprises the aforementioned organic semiconductor material, a second carrier transfer layer and a second electrode. Wherein, the second carrier transfer layer is disposed between the active layer and the second electrode.

In one embodiment, when X1 and X2 are selected from the group consisting of Si, Ge and derivatives thereof, the active layer further comprises an organic solvent, and the solubility of the organic solvent to the active layer is not less than 5 mg/mL.

In one embodiment, when X1 and X2 are selected from one of C and its derivative, the active layer further comprises an additive having at least one characteristic of being a poor solvent for at least one of an electron donor and an electron acceptor in the active layer, and boiling point of the additive being higher than a process solvent of manufacturing the organic photoelectric device.

Compared with the prior art, the organic semiconductor material of the present invention can effectively improve the power conversion efficiency of the organic photoelectric device. Even with a variety of different electron donor materials, the power conversion efficiency of the organic photoelectric device can reach to 10%, and the highest can be more than 14%.

BRIEF DESCRIPTION OF THE APPENDED DRAWINGS

Some of the embodiments will be described in detail, with reference to the following figures, wherein like designations denote like members, wherein.

Figure 1:
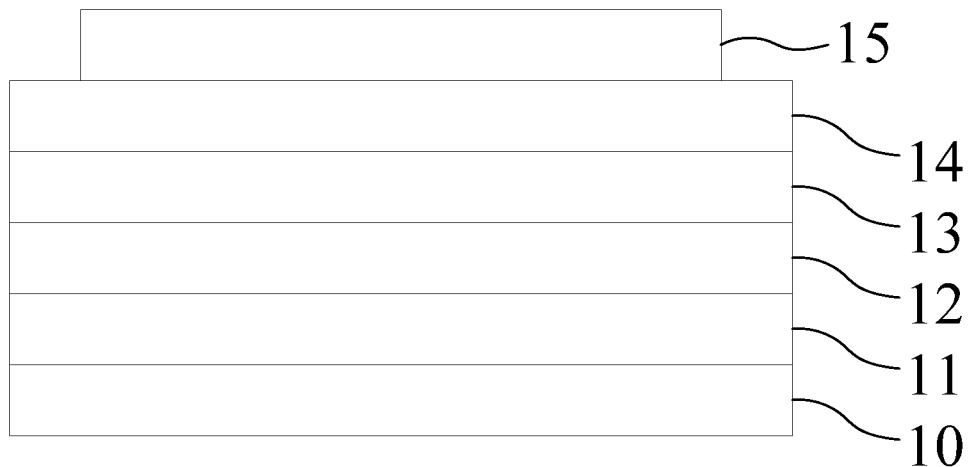
FIG. 1 shows a schematic structural diagram of one embodiment of an organic photoelectric device of the present invention.

The advantages, spirits, and features of the present invention will be explained and discussed with embodiments and figures as follows.

DETAILED DESCRIPTION OF THE INVENTION

In order to make the advantages, spirit and features of the present invention easier and clearer, it will be detailed and discussed in the following with reference to the embodiments and the accompanying drawings. It is worth noting that the specific embodiments are merely representatives of the embodiments of the present invention, but it can be implemented in many different forms and is not limited to the embodiments described in this specification. Rather, these embodiments are provided so that this disclosure will be thorough and complete.

The terminology used in the various embodiments disclosed in the present invention is only for the purpose of describing specific embodiments, and is not intended to limit the various embodiments disclosed in the present invention. As used herein, singular forms also include plural forms unless the context clearly indicates otherwise. Unless otherwise defined, all terms (including technical and scientific terms) used in this specification have the same meanings as commonly understood by one of ordinary skill in the art to which the various embodiments disclosed herein belong. The above terms (such as those defined in commonly used dictionaries) will be interpreted as having the same meaning as the contextual meaning in the same technical field, and will not be interpreted as having an idealized or overly formal meaning, unless explicitly defined in the various embodiments disclosed herein.

In the description of this specification, the description of the reference terms "an embodiment", "a specific embodiment" and the like means that specific features, structures, materials, or characteristics described in connection with the embodiment are included in at least one embodiment of the present invention. In this specification, the schematic expressions of the above terms do not necessarily refer to the same embodiment. Furthermore, the particular features, structures, materials, or characteristics described may be combined in any suitable manner in any one or more embodiments.

Definition

As used herein, "donor" material refers to a semiconductor material, such as an organic semiconductor material, having electron holes as a primary current or charge carrier. In some embodiments, when a p-type semiconductor material is deposited on a substrate, it can provide the electron holes with a hole mobility greater than about $10^{-5}$ cm$^2$/Vs. In the case of field effect devices, current on/off ratio of the p-type semiconductor material exhibits more than about 10.

As used herein, "acceptor" material refers to the semiconductor material, such as the organic semiconductor material, having electrons as the primary current or the charge carrier. In some embodiments, when a n-type semiconductor material is deposited on a substrate, it can provide the electrons with an electron mobility greater than about $10^{-5}$ cm$^2$/Vs. In the case of field effect devices, current on/off ratio of the n-type semiconductor material exhibits more than about 10.

As used herein, "mobility" refers to a speed rate of the charge carrier moving through the material under the influence of an electric field. The charge carrier is the electron hole (positive charge) in the p-type semiconductor material and the electron (negative charge) in the n-type semiconductor material. This parameter depends on architecture of component and can be measured by field effect component or space charge limiting current.

The compound as used herein is considered as "environmentally stable" or "stabilized under ambient conditions" and refers to that the carrier mobility of the transistor of the semiconductor material utilized the compound is maintained at initial value while the transistor has been exposed to an environmental condition such as air, environmental temperature and humidity for a duration. For example, a compound may be considered to be environmentally stable if the change in carrier mobility of a transistor incorporating the compound is less than 20% or 10% of the initial value after being exposed to the environmental conditions including air, humidity and temperature for 3, 5 or 10 days.

Fill factor (FF) used herein refers to the ratio of the actual maximum available power ($P_m$ or $V_{mp}*J_{mp}$) to the theoretical (non-actually available) power ($J_{sc}*V_{oc}$). Therefore, the fill factor can be determined by the following formula:

$$FF=(V_{mp}*J_{mp})/(V_{oc}*J_{sc})$$

Wherein, the $J_{mp}$ and $V_{mp}$ respectively represent the current density and voltage at the maximum power point ($P_m$), which is obtained by varying the resistance in the circuit to the maximum value of J*V. $J_{sc}$ and $V_{oc}$ represent open circuit current and open circuit voltage, respectively. The fill factor is a key parameter for evaluating solar cells. The fill factor of commercial solar cells is typically greater than about 0.60%.

The open circuit voltage ($V_{oc}$) used herein is the potential difference between the anode and the cathode of the component without connecting the external load.

The power conversion efficiency (PCE) of solar cells used herein refers to the conversion percentage of power from the incident light to the electricity power. The power conversion efficiency (PCE) of solar cells can be calculated by dividing the maximum power point ($P_m$) by the incident light irradiance (E; W/m$^2$) under the standard test conditions (STC) and the surface area (Ac; m$^2$) of the solar cells. STC generally refers to the conditions of temperature of 25° C., irradiance of 1000 W/m$^2$, and air mass (AM) 1.5 spectrum.

The member (e.g., a thin film layer) as used herein can be considered as "photoactive" if it contains one or more compounds capable of absorbing photons to generate excitons for producing photocurrents.

As used herein, "solution proceeding" refers to a process in which a compound (e.g., a polymer), material, or composition can be used in a solution state, such as spin coating, printing (e.g., inkjet printing, gravure printing, and lithography printing), spray coating, slit coating, drop casting, dip coating, and knife coating.

As used herein, "annealing" refers to a post-deposition heat treatment to a semi-crystalline polymer film for certain duration in the environment or under decompressed or pressurized environment. "Annealing temperature" refers to the temperature at which the polymer film or the mixed film of the polymer and other molecules can perform small-scale molecular movement and rearrangement during the annealing process. Without limitation by any particular theory, it is believed that annealing can lead to an increase in crystallinity in the polymer film, enhance the material carrier mobility of the polymer film or a mixed film of the polymer with other molecules, and the molecules are arranged alternately to achieve the effect of independent transmission paths of effective electrons and holes.

As used herein, "halo" or "halogen" means fluoro, chloro, bromo and iodo.

As used herein, "alkyl" refers to a straight or branched saturated hydrocarbon. For example, alkyl includes methyl (Me), ethyl (Et), propyl (e.g. n-propyl and iso-propyl), butyl (e.g. n-butyl, iso-butyl, t-butyl, and tert-butyl), pentyl (e.g. n-pentyl and iso-pentyl), hexyl, and the like. In various embodiments, the alkyl can have 1 to 40 carbon atoms (i.e., C1-40 alkyl), such as 1 to 30 carbon atoms (i.e., C1-30 alkyl). In some embodiments, the alkyl can have 1 to 6 carbon atoms and can be referred to as a "lower alkyl." For example, the lower alkyl includes methyl, ethyl, propyl (e.g., n-propyl and iso-propyl), and butyl (e.g., n-butyl, iso-butyl, t-butyl, and tert-butyl). In some embodiments, alkyl can be substituted as described herein. Generally, Alkyl would not be substituted by another alkyl, alkenyl or alkynyl.

Substituted alkyl groups may, depending on the length of the alkyl chain, have one or more (e.g. 1, 2, 3, 4, 5 or more than 5) substituents. Preferably, each is independently selected from alkyl, aryl, heteroaryl, fluorine, chlorine, bromine, hydroxyl, mercapto, cyano, nitro, nitroso, formyl, naphthyl, carboxylate, alkylcarbonyloxy, carbamoyl, sulfonate, sulfamino, sulfamide, amidino, cycloalkyl, heterocycloalkyl, and the like substituents. These substituents are the substituents mentioned above for these groups.

The above remarks regarding unsubstituted and substituted alkyl also apply to unsubstituted and substituted alkoxy. As used herein, "alkenyl" refers to straight or branched carbon chain having one or more carbon-carbon double bonds. For example, alkenyl includes vinyl, propenyl, butenyl, pentenyl, hexenyl, butadienyl, pentadienyl, hexadienyl and the like. One or more carbon-carbon double bond may be located in internal (e.g., 2-butene) or terminal (e.g., 1-butene). In various embodiments, alkenyl can have 2 to 40 carbon atoms (i.e., C2-40 alkenyl) or 2 to 20 carbon atoms (i.e., C2-20 alkenyl). In some embodiments, alkenyl can be substituted as described herein. Generally, Alkenyl would not be substituted by another alkenyl, alkyl or alkynyl.

As used herein, "fused ring" or "fused ring group" refers to a polycyclic system having at least two rings, and at least one of which is an aromatic ring, wherein the aromatic ring (carbocyclic or heterocyclic) shares a bond with at least one aromatic or non-aromatic ring (carbocyclic or heterocyclic). The polycyclic systems can be highly π-conjugated systems as described herein, or be selectively substituted as described herein.

As used herein, "heteroatom" means an atom of any element other than carbon and hydrogen, such as nitrogen, oxygen, helium, sulfur, phosphorus, and selenium.

As used herein. "aryl" refers to an aromatic monocyclic hydrocarbon ring system, or polycyclic ring system which is fused by one or more aromatic hydrogen rings, or fused by at least one aromatic monocyclic hydrocarbon ring with one or more cycloalkyl rings and/or heterocyclic rings. The aryl may contain 6 to 24 carbon atoms (e.g., C6-C24 aryl) and may include a plurality of fused rings. In some embodiments, the polycyclic aromatic group can have 8 to 24 carbon atoms. Any suitable ring position in the aryl can be covalently bonded to a defined chemical structure. Examples of the aromatic groups having an aromatic carbocyclic ring include phenyl, 1-naphthyl (bicyclic), 2-naphthyl (bicyclic), fluorenyl (tricyclic), phenanthryl (tricyclic), and pentacyl (five rings) and so on. Examples of the polycyclic system in which at least one aromatic monocyclic hydrocarbon ring is fused to one or more cycloalkyl rings and/or heterocyclic rings, comprises benzene derivatives containing cyclopentane (i.e., fluorenyl, and 5,6-bicycloalkyl/aromatic ring system), benzene derivatives containing cyclohexane (i.e., tetrahydronaphthyl, and 6,6-biscycloalkane/aromatic ring system), benzene derivatives containing imidazolines (i.e., benzimidazolinyl, 5,6-bicyclic heterocyclyl/aromatic ring system), and benzene derivatives containing pyran (i.e., benzopyranyl, and 6,6-bicyclic heterocyclic/aromatic ring system). Other examples of aryl group include benzodioxanyl, benzodioxolyl, chromanyl, porphyrin, and the like. In some embodiments, aryl can be substituted as described herein. In some embodiments, aryl can have one or more halogen substituent and can also be referred to as halogen aryl. Perhaloaryl, which is included in the halogen substituent, is that all of hydrogen atoms in aryl are replaced by halogen atom (for example, $C_6F_5$). In certain embodiments, one of the substituent of the aryl is substituted with another aryl and may be referred to as diaryl. Each aryl of diaryl can be substituted as disclosed herein.

As used herein, "heteroaromatic" refers to an aromatic monocyclic system containing ring heteroatom selected from the group consisting of oxygen (O), nitrogen (N), sulfur (S), cerium (Si), and selenium (Se), or a polycyclic system with at least one ring which is aromatic and containing at least one ring heteroatom. Polycyclic heteroaryl contains one or more aromatic carbocyclic ring, non-aromatic carbocyclic ring and/or non-aromatic heterocyclic rings. Heteroaryl may have, for example, aromatic ring containing 5 to 24 atoms, wherein the atoms including 1 to 5 hetero atoms (such as heteroaryl containing 5 to 20 members). Heteroaryl can be attached to a defined chemical structure at any heteroatom or carbon atom to form stable structure. Heteromatic ring usually does not contain linkages of O—O, S—S or S—O. However, one or more N or S atoms of the heteroaromatic may be oxidized (e.g., pyridine N-oxide, thiophene S-oxide, thiophene S, and S-dioxide). Examples of heteroaromatic includes monocyclic of 5 or 6 members and 5-6 bicyclic systems, wherein heteroaromatic may contain O, S, NH, N-alkyl, N-aryl, N-(arylalkane) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaromatic rings include pyrrolyl, furyl, thienyl, pyridyl, pyrimidinyl, pyridazinyl, pyrazinyl, triazolyl, tetrazolyl, pyrazolyl imidazolyl, isothiazolyl, thiazolyl, thiadiazolyl, isoxazolyl, oxazolyl, oxadiazolyl, fluorenyl, isodecyl, benzofuranyl, benzothienyl, quinolinyl, 2-methylquinolyl, isoquinolyl, quinoxalyl, quinazolyl, benzotriazolyl, benzimidazolyl, benzothiazolyl, benzene isothiazolyl, benzisoxazole, benzoxazolyl, benzoxazolyl, cinnolinyl, 1H-carbazolyl, 2H-carbazolyl, indolizinyl, isobenzofuranyl, naphthyridinyl, phthalazinyl, pteridinyl, purinyl, oxazolopyridinyl, thiazolopyridyl, Imidazopyridyl, furopyridinyl, thienopyridyl, pyridopyrimidinyl, pyridopyrazinyl, pyridopyridazinyl, thienothiazolyl, thienooxazolyl, thienoimidazolyl, and the like. Further, examples of heteroaromatic include 4,5,6,7-tetrahydroindenyl, tetrahydroquinolyl, benzothienopyridinyl, benzofuropyridinyl, and the like. In some embodiments, heteroaryl can be substituted as disclosed herein.

Substituted cycloalkyl groups may, depending on the ring size, have one or more (e.g. 1, 2, 3, 4, 5 or more than 5) substituents. Preferably, each is independently selected from cycloalkyl, carbonylalkyl, aryl, heteroaryl, fluorine, chlorine, bromine, hydroxyl, mercapto, cyano, nitro, nitroso, formyl, acyl, carboxylate, alkylcarbonyloxy, carbamoyl, sulfonate, sulfamino, sulfamide, amidino.

In order to solve the problems in the prior art, the present invention provides an organic semiconductor material for an active layer, which can effectively increase the power conversion efficiency of an organic photoelectric device. In one embodiment, the organic semiconductor material of the present invention comprises the following structure of formula I:

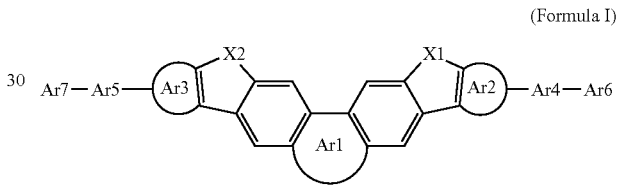

(Formula I)

Wherein, X1 and X2 can be the same or different, and X1 and X2 are independently selected from one of the following: C, Si, Ge and derivatives thereof; Ar1 is selected from the group consisting of five-member heterocyclic ring with and without substitutions, and six-member heterocyclic ring with and without substitutions; Ar2 and Ar3 can be the same or different, and Ar2 and Ar3 are independently selected from the group consisting of aromatic ring with and without substitutions, heterocyclic ring with and without substitutions, fused ring with and without substitutions and fused heterocyclic ring with and without substitutions, wherein Ar2 and Ar3 include at least one of five-member ring and six-member ring, and the number of the rings is 1 to 3; Ar4 and Ar5 can be the same or different, and Ar4 and Ar5 are independently selected from the group consisting of aromatic ring with and without substitutions, heterocyclic ring with and without substitutions, fused ring with and without substitutions and fused heterocyclic ring with and without substitutions, wherein Ar4 and Ar5 include at least one of five-member ring and six-member ring, and the number of the rings is 0 to 3; Ar6 and Ar7 can be the same or different, and Ar6 and Ar7 are independently selected from the group consisting of electron-withdrawing aromatic ring with and without substitutions, electron-withdrawing heterocyclic ring with and without substitutions, electron-withdrawing fused ring with and without substitutions and electron-withdrawing fused heterocyclic ring with and without substitutions; Ar6 bonds to Ar2 or Ar4 with sing bond or double bond; and Ar7 bonds to Ar3 or Ar5 with sing bond or double bond.

In practice, the substitution of the formula I is selected from the group consisting of: C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

In one embodiment, Ar1 of the formula I comprises the structure of formula II:

(Formula II)

Wherein, X3 is selected from one of following: C, S, Se, Te, NR1, CR1$_2$ and SiR1$_2$, and R1 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

In one embodiment, Ar1 of the formula I comprises the structure of formula III:

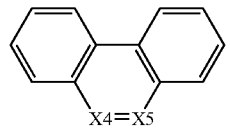

(Formula III)

Wherein, X4 and X5 can be the same or different, and X4 and X5 are independently selected from the following: C, N, CR2 and NR2, and R2 is selected from the group consisting of C1-C30 alkyl, C1-C30 branched alkyl, C1-C30 silyl, C1-C30 ester, C1-C30 alkoxy, C1-C30 alkylthio. C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

In practice, Ar2 and Ar3 of the formula I are independently selected from the following structure:

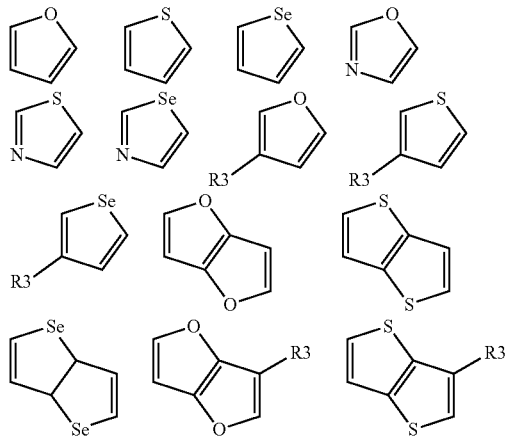

-continued

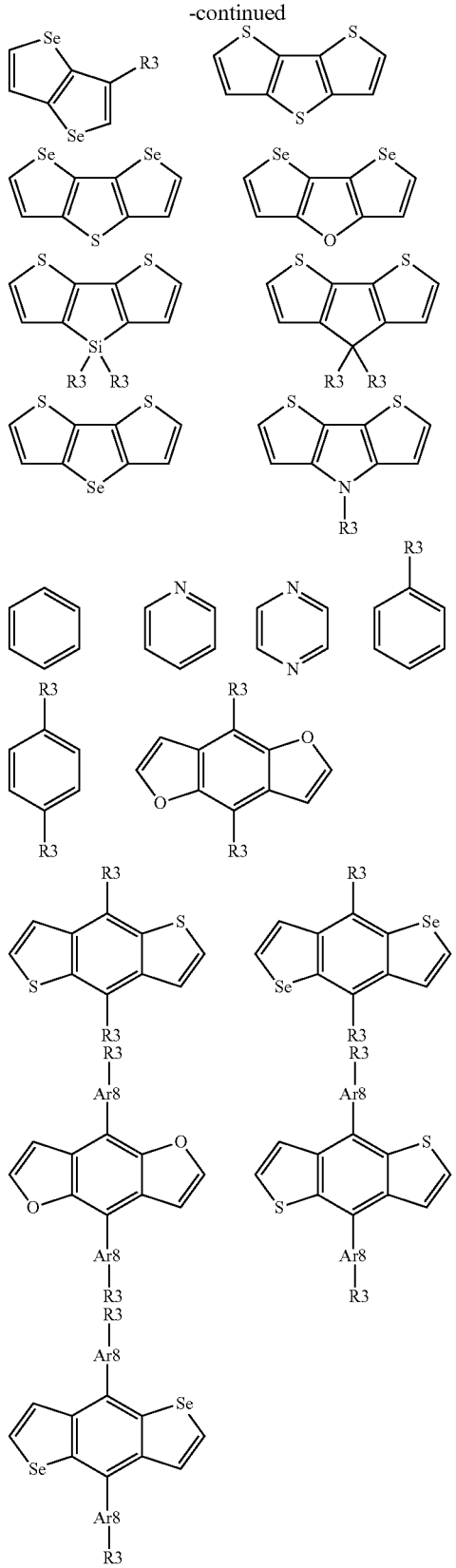

Wherein, R3 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen; and Ar8 is selected from the group consisting of aromatic ring with and without substitutions, heterocyclic ring with and without substitutions, fused ring with and without substitutions and fused heterocyclic ring with and without substitutions.

In practice, Ar4 and Ar5 of the formula I are independently selected from the following structure:

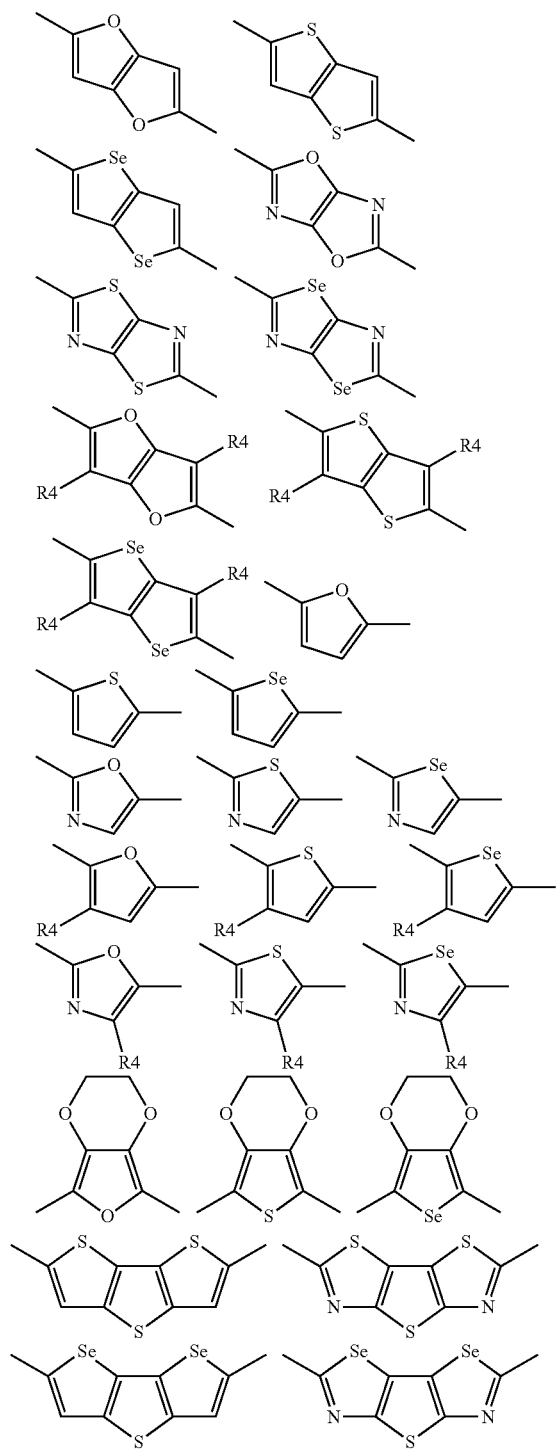

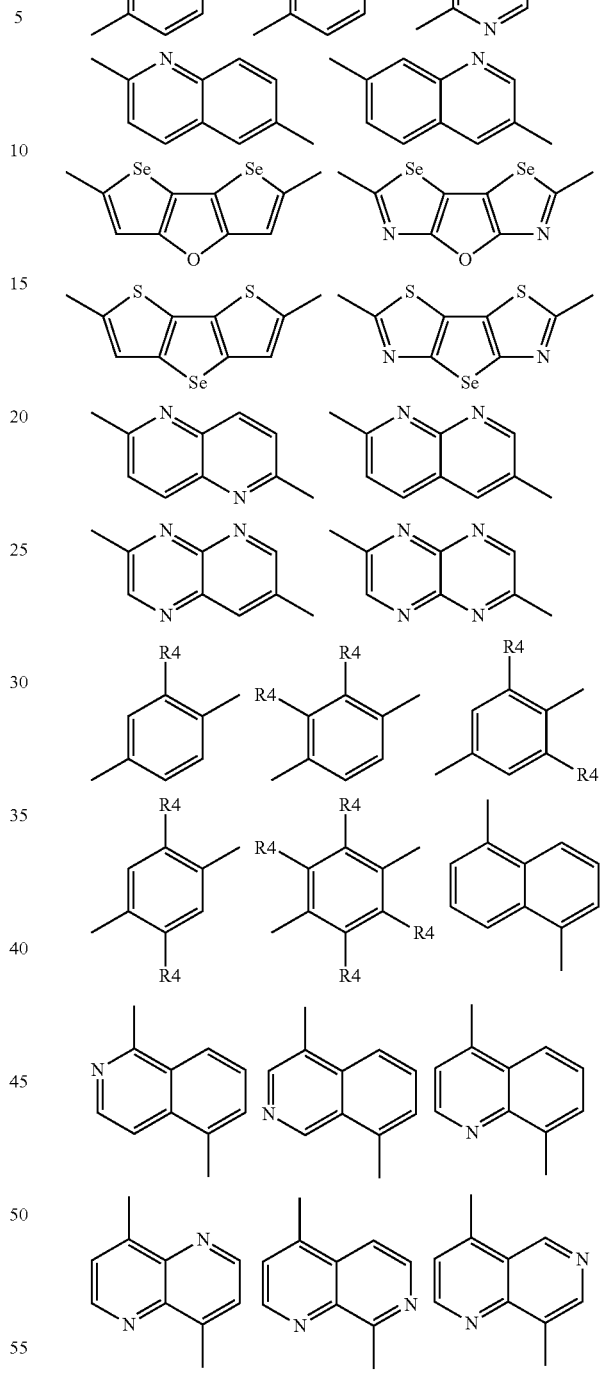

Wherein, R4 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

In practice, Ar6 and Ar7 of the formula I are independently selected from the following structure:

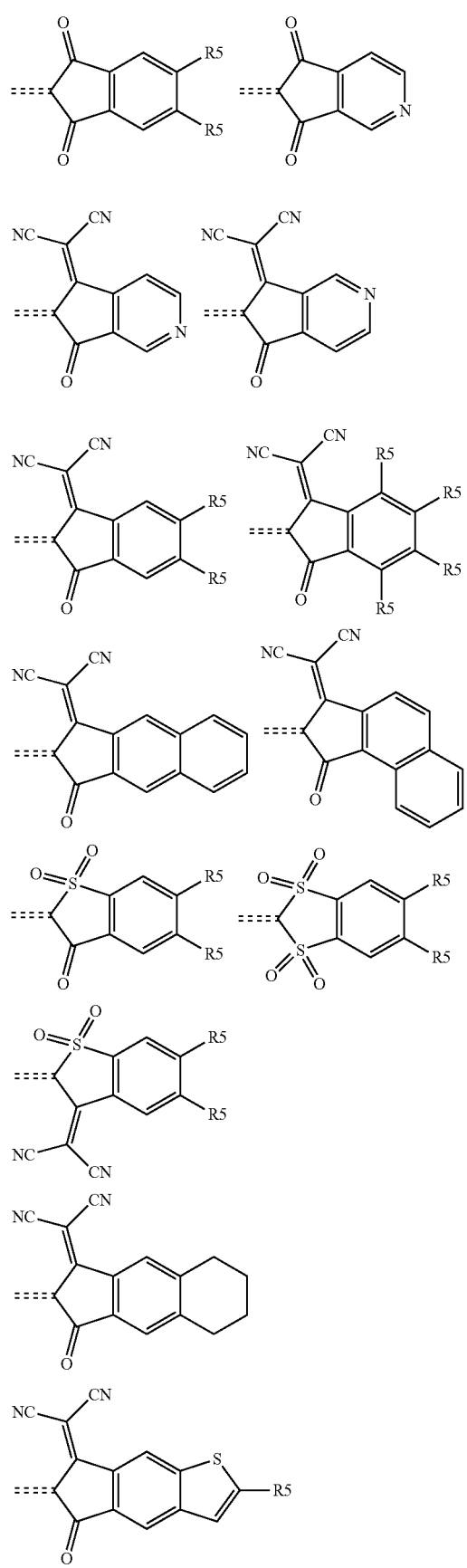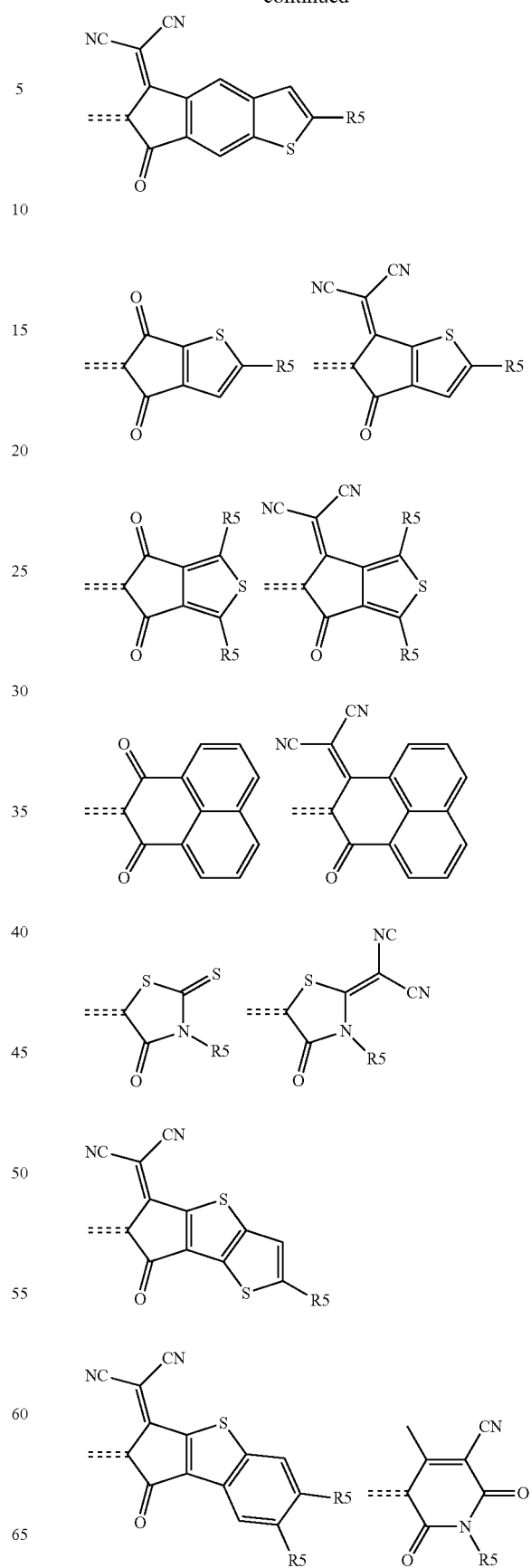

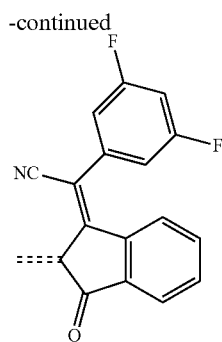

Wherein, R5 is selected from the group consisting of C1-C20 alkyl, C1-C20 alkoxy, C1-C20 carbonyl. C1-C20 ester, cyano, oxygen, hydrogen, and halogen.

Please referring to FIG. 1, FIG. 1 shows a schematic structural diagram of one embodiment of an organic photoelectric device of the present invention. As shown in FIG. 1. In another embodiment, the present invention further provides an organic photoelectric device 1, which comprises a first electrode 11, a second electrode 15 and an active layer 13. The active layer 13, which includes the aforementioned organic semiconductor material, is disposed between the first electrode 11 and the second electrode 15. In practice, the organic photoelectric device 1 may have a laminated structure, which sequentially includes a substrate 10, the first electrode 11 (transparent electrode), an electron transfer layer (ETL) 12, the active layer 13, a hole transfer layer (HTL) 14 and the second electrode 15. In addition, the organic photoelectric device 1 may include an organic photovoltaic device, an organic light sensing device, an organic light emitting diode, and an organic thin film transistor (OTFT).

In practice, the active layer of the organic photoelectric device of the present invention includes the organic semiconductor material including formula I described above.

Preparation of the Active Layer:
Synthesis steps of DTCC-4Cl, DTSC-4Cl, DTSC-4F.
Synthesis of Compound 2:

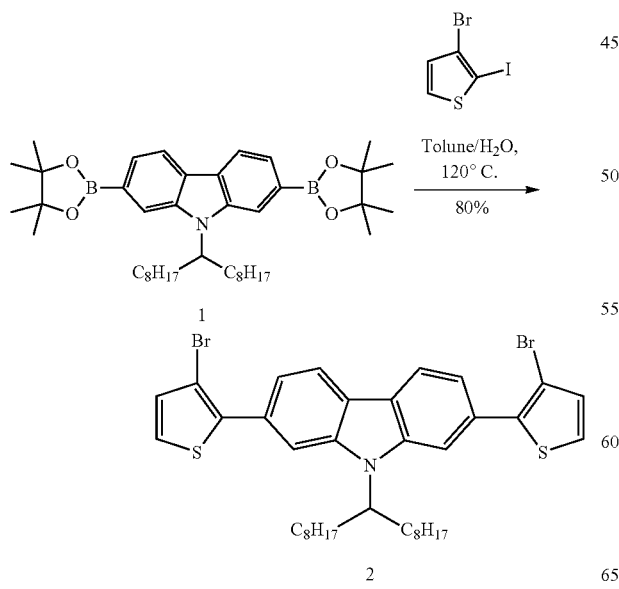

Compound 1 (0.30 g, 0.47 mmol), 3-bromo-2-iodothiophene (0.32 g, 1.11 mmol), $K_2CO_3$ (0.39 g, 2.82 mmol), Aliquant 336 (0.05 g, 0.12 mmol), and $Pd(PPh_3)_4$ (54 mg, 0.047 mmol) were dissolved in deoxygenated toluene/$H_2O$ (12 mL, 5:1, v/v). The reaction mixture was refluxed at 120° C. for 72 h and then extracted with diethyl ether (50 mL×3) and water (50 mL). The collected organic layer was dried over $MgSO_4$. After removal of the solvent under reduced pressure, the residue was purified by column chromatography on silica gel (hexane/ethyl acetate, v/v, 30/1) to give a pale yellow sticky product 2 (0.30 g, 88%). $^1$H NMR ($CDCl_3$, 400 MHz, ppm): δ 0.77-0.90 (m, 6H), 1.02-1.25 (m, 24H), 1.89-1.98 (m, 2H), 2.28-2.39 (m, 2H), 4.58-4.64 (m, 1H), 7.11 (d, J=5.4 Hz, 2H), 7.31 (d, J=5.4 Hz, 2H), 7.45 (dd, J 1=8.1 Hz, J 2=1.2 Hz, 2H), 7.76 (br, 1H), 7.97 (br, 1H), 8.11 (br, 2H); 13 C NMR (CDCl3, 75 MHz, ppm): δ 14.20, 22.73, 26.96, 29.30, 29.47, 29.53, 31.89, 33.99, 56.79, 107.43, 109.77, 112.23, 120.29, 120.42, 120.69, 122.16, 123.54, 125.04, 129.87, 130.45, 131.91, 139.11, 139.54, 142.59, 158.01; MS (FAB, $C_{37}H_{45}Br_2NS_2$): calcd, 727.70; found, 728.

Synthesis of Compound 3

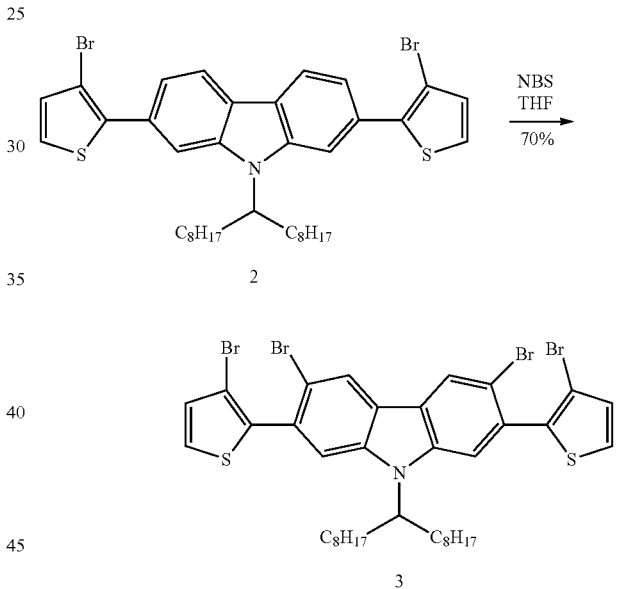

N-Bromosuccimide (0.38 g, 2.12 mmol) was added in one portion to a solution of 2 (0.67 g, 0.92 mmol) in acetone (15 mL). The reaction was stirred under dark for 12 h at room temperature. The mixture solution was extracted with diethyl ether (50 mL×3) and water (50 mL). The combined organic layer was dried over $MgSO_4$. After removal of the solvent under reduced pressure, the residue was purified by column chromatography on silica gel (hexane) to give a pale yellow sticky product 3 (0.55 g, 68%). $^1$H NMR ($CDCl_3$, 400 MHz, ppm): δ 0.79-0.90 (m, 6H), 0.95-1.25 (m, 24H), 1.82-1.90 (m, 2H), 2.17-2.28 (m, 2H), 4.44-4.51 (m, 1H), 7.11 (d, J=5.4 Hz, 2H), 7.43 (d, J=5.4 Hz, 2H), 7.46 (br, 1H), 7.62 (br, 1H), 8.35 (d, J=6.9 Hz, 2H); $^{13}$C NMR ($CDCl_3$, 75 MHz, ppm): δ 14.21, 15.42, 22.73, 26.77, 29.24, 29.39, 29.41, 31.86, 33.75, 57.17, 65.99, 111.48, 113.59, 114.59, 115.98, 123.23, 124.62, 124.93, 126.27, 130.18, 130.80, 131.35, 138.04, 138.22, 141.55; MS (FAB, $C_{37}H_{43}Br_4NS_2$): calcd, 885.49; found, 886.

Synthesis of Compound 4

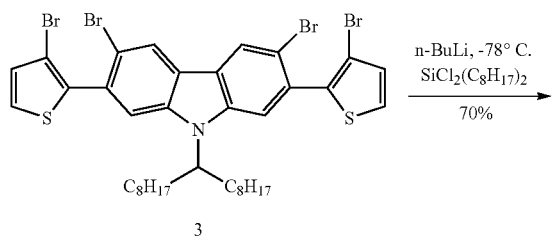

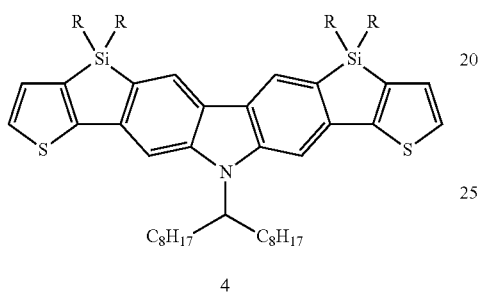

A 2.5 M solution of n-Butyllithium (n-BuLi) in hexane (7.46 mL, 18.65 mmol) was added dropwise to a solution of 3 (3.12 g, 3.52 mmol) in dry THF (82 mL) at −78° C. After stirring at −78° C. for 1 h and room temperature for 1 h, Di-n-octyldichlorosilane (3.53 g, 10.84 mmol) was introduced by syringe to the solution at −78° C. The mixture solution was warmed up to room temperature and stirred for 15 h. The mixture solution was quenched with water and extracted with diethyl ether (50 mL×3) and water (50 mL). The combined organic layer was dried over MgSO₄. After removal of the solvent under reduced pressure, the residue was purified by column chromatography on silica gel (hexane) to give a green sticky product 4 (1.05 g, 27.77%). ¹H NMR (CDCl₃, 400 MHz, ppm): δ 0.7-0.9 (m, 16H), 0.94-1.5 (m, 82H), 1.95-2.09 (m, 2H), 2.25-2.34 (m, 2H), 4.53-4.68 (m, 1H), 7.12-7.18 (m, 1H), 7.28-7.32 (m, 1H) 7.41-7.48 (s, 1H), 7.58-7.64 (s, 1H), 8.15-8.21 (s, 2H); MS (FAB, C69H111NS2Si2): calcd, 1073.7; found, 1073.8.

Synthesis of Compound 5:

A mixture of compound 4 (320 mg, 0.29 mmol) and 1,2-dichloroethane (20 mL) was deoxygenated with nitrogen for 30 min and then added a solution of POCl₃ (0.13 mL) in DMF (1.36 mL) at 0° C. After being stirred at 60° C. for 20 hours, the mixture was poured into Na₂CO₃(aq) and extracted with CH₂Cl₂. The organic layer was washed with water, and then dried over anhydrous MgSO₄. After the removal of solvent, the residue was purified by column chromatography on silica gel using n-hexane/CH₂Cl₂ (1:1) as eluent to give product 5 as an yellow solid (240 mg, 73%). ¹H NMR (CDCl₃, 400 MHz, ppm): δ 0.7-0.9 (m, 16H), 0.94-1.5 (m, 82H), 1.95-2.09 (m, 2H), 2.25-2.34 (m, 2H), 4.53-4.68 (m, 1H), 7.56-7.61 (s, 1H), 7.73-7.77 (s, 1H), 7.79-7.83 (s, 2H), 8.20-8.30 (d, J=8 Hz, 2H), 9.91-9.96 (s, 2H).

Synthesis of DTSC-4F:

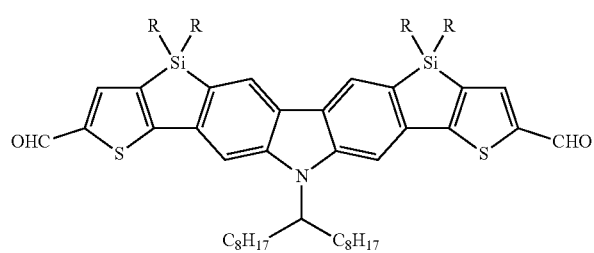

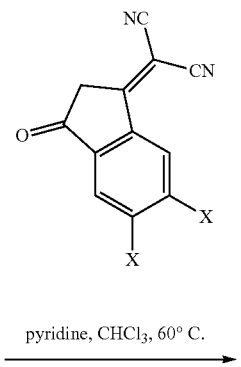

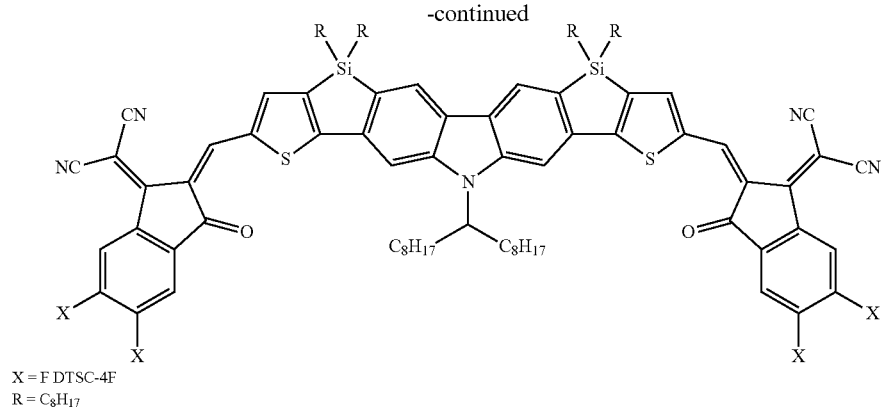

X = F DTSC-4F
R = C8H17

A mixture of compound 5 (240 mg, 0.21 mmol), 2-(5,6-difluoro-3-oxo-2,3-dihydro-1H-inden-1-ylidene)malononitrile (240 mg, 1.05 mmol) in CHCl₃ (15.5 mL) was deoxygenated with nitrogen for 30 minutes. Pyridine (0.3 mL) was added and refluxed for 24 hours. After the mixture was cooled to room temperature, the mixture was poured into water (100 mL) and extracted with CH₂Cl₂. The organic layer was washed with water, and then dried over anhydrous MgSO₄. After the removal of solvent, the residue was purified by column chromatography on silica gel using n-hexane/CH₂Cl₂ (1:1) as eluent to give DTSC-4F as a dark blue solid (190 mg, 58%). ¹H NMR (CDCl₃, 400 MHz, ppm): δ 0.72-0.87 (m, 16H), 0.97-1.50 (m, 82H), 2.05-2.16 (m, 2H), 2.28-2.43 (m, 2H), 4.64-4.72 (m, 1H), 7.68-7.77 (q, J=8 Hz), 7.82-7.86 (s, 1H), 7.91-7.97 (m, 3H), 8.27-8.30 (s, 1H), 8.31-8.34 (s, 1H), 8.54-8.61 (m, 2H), 8.99-9.03 (s, 2H); MS (FAB, C95H115F4N5O2S2Si2): calcd, 1553.8; found, 1554.7.

Synthesis of DTSC-4Cl:

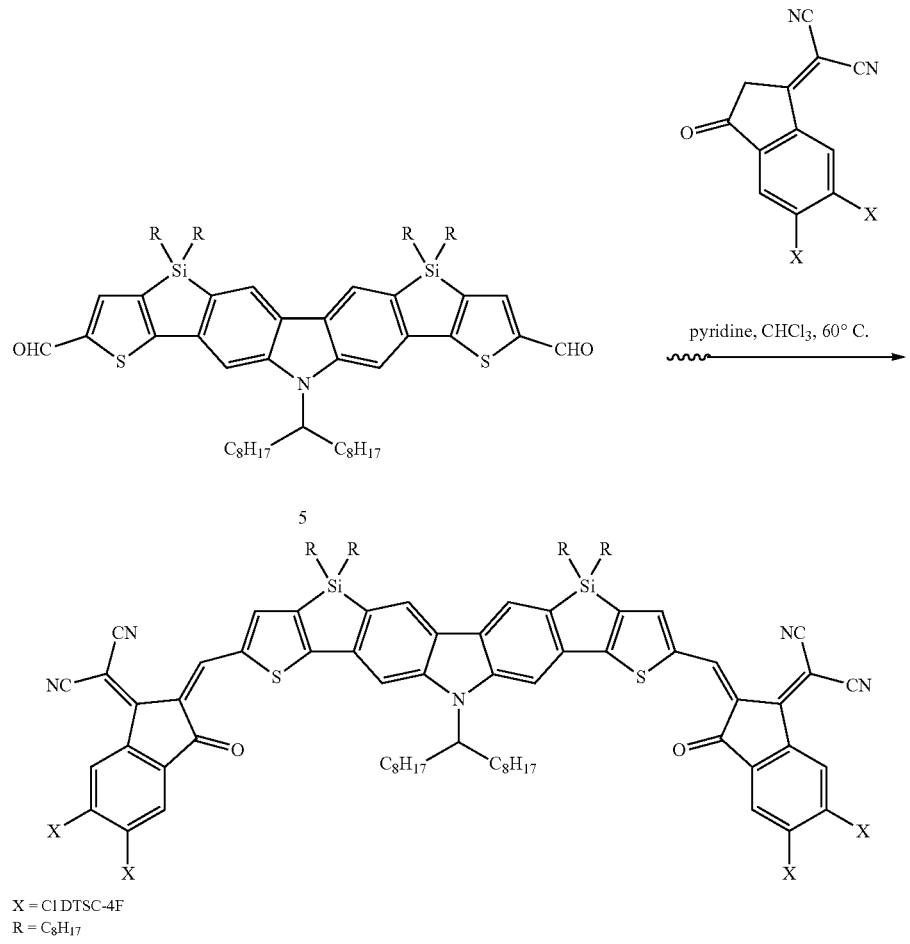

5

X = Cl DTSC-4F
R = C8H17

A mixture of compound 5 (50 mg, 0.044 mmol), 2-(5,6-dichloro-3-oxo-2,3-dihydro-1H-inden-1-ylidene)malononitrile (58 mg, 0.22 mmol) in CHCl$_3$ (15.5 mL) was deoxygenated with nitrogen for 30 minutes. Pyridine (0.25 mL) was added and refluxed for 17 hours. After the mixture was cooled to room temperature, the mixture was poured into water (100 mL) and extracted with CH$_2$Cl$_2$. The organic layer was washed with water, and then dried over anhydrous MgSO$_4$. After the removal of solvent, the residue was purified by column chromatography on silica gel using n-hexane/CH$_2$Cl$_2$ (1:1) as eluent to give DTSC-4Cl as a dark blue solid (66 mg, 92%). $^1$H NMR (CDCl$_3$, 400 MHz, ppm): δ 0.74-0.89 (m, 16H), 0.98-1.4 (m, 82H), 2.03-2.18 (m, 2H), 2.29-2.42 (m, 2H), 4.64-4.72 (m, 1H), 7.85 (s, 1H), 7.96 (t, 3H), 8.00 (s, 1H), 8.29-8.33 (d, 2H), 8.8 (s, 1H), 3.09 (s, 2H); MS (FAB, C$_{95}$H$_{115}$Cl$_4$N$_5$O$_2$S$_2$Si$_2$): calcd, 1621.09; found, 1621.13.

Synthesis of DTSC-4Cl:

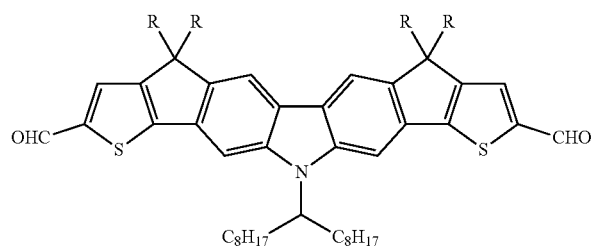

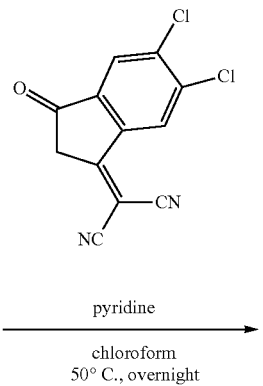

pyridine
chloroform
50° C., overnight

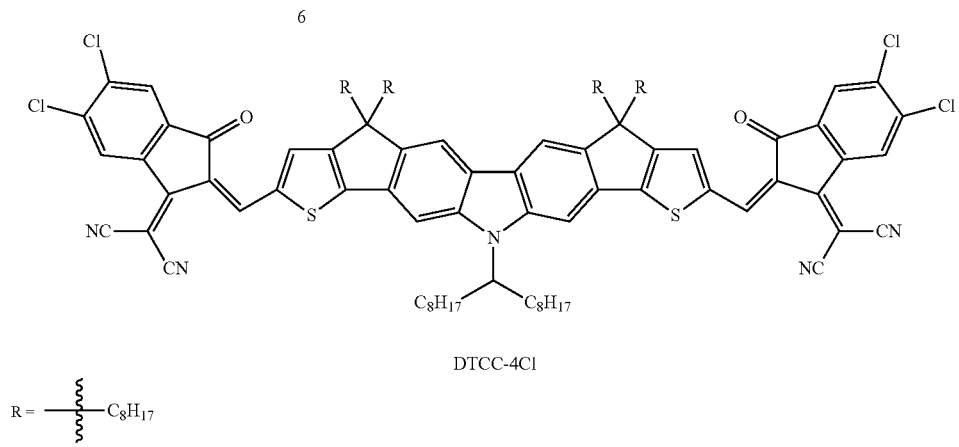

DTCC-4Cl

R = —$C_8H_{17}$

A mixture of compound 6 (300 mg, 0.27 mmol), 2-(5,6-dichloro-3-oxo-2,3-dihydro-1H-inden-1-ylidene)malononitrile (359 mg, 1.35 mmol) in CHCl$_3$ (20 mL) was deoxygenated with nitrogen for 30 minutes. Pyridine (0.3 mL) was added and then refluxed for 24 hours. After the mixture was cooled to room temperature, the mixture was poured into water (100 mL) and extracted with CH$_2$Cl$_2$. The organic layer was washed with water, and then dried over anhydrous MgSO$_4$. After removal (1:2) as eluent to give DTCC-4Cl as a dark blue solid (325 mg, 75%), $^1$H NMR (400 MHz, CDCl$_3$): δ9.02-9.03 (d, 2H), 8.79 (s, 2H), 8.04 (s, 1H), 8.00 (s, 1H), 7.95 (s, 2H), 7.83 (s, 1H), 7.74-7.76 (d, 2H), 7.69 (s, 1H), 4.57-4.63 (m, 1H), 2.29-2.32 (m, 2H), 1.97-2.17 (m, 10H), 1.13-1.36 (m, 64H), 0.9 (m, 8H), 0.79 (t, 18H). HRMS (FAB) Calcd for C$_{97}$H$_{115}$C$_{14}$N$_5$O$_2$S$_2$ [M]$^+$, 1585.7246; found 1585.7248.

The active layer includes an electron acceptor and an electron donor, wherein the electron acceptor is the aforementioned organic semiconductor material, and DTCC-4Cl, DTSC-4Cl, DTSC-4F are taken as exampled below.

A glass coated by a pre-patterned Indium Tin Oxides (ITO) with a sheet resistance of ~15 Ω/sq is used as a substrate. The substrate is ultrasonically oscillated in soap deionized water, deionized water, acetone, and isopropanol in sequence, and washed in each step for 15 minutes. The washed substrate is further treated with a UV-ozone cleaner for 30 minutes. A top coating layer of ZnO (diethylzinc solution, 15 wt % in toluene, diluted with tetrahydrofuran) is spin coated on the ITO substrate with a rotation rate of 5000 rpm for 30 seconds, and then baked at 150° C. in air for 20 minutes. The active layer solution was prepared in o-xylene. The active layer includes the aforementioned organic semiconductor material. To completely dissolve the active layer material, the active layer solution is stirred on a hot plate at 120° C. for at least 1 hour. Then, the active layer material is returned to the room temperature for spin coating. Finally, the thin film formed by the coated active layer is annealed at 120° C. for 5 minutes, and then transferred to a thermal evaporation machine. A thin layer (8 nm) of MoO$_3$ is deposited as an anode intermediate layer under a vacuum of 3×10$^{-6}$ Torr, and then a silver layer with a thickness of 100 nm is deposited as an upper electrode. All batteries are encapsulated with epoxy resin in the glove box to make organic electronic components (ITO/ETL/active layer/MoO$_3$/Ag). The J-V characteristics of the components is measured by a solar simulator (having a xenon lamp with an AM 1.5 G filter) in air and at room temperature and under AM 1.5 G (100 mW cm$^2$). Herein, a standard ruthenium dipole with a KG5 filter is used as a reference cell to calibrate the light intensity to make the mismatch portion of the spectrum consistent. The J-V characteristics are recorded by a Keithley 2400 source meter instrument. A typical battery has an element area of 4 mm$^2$, which is defined by the area of the metal mask aligning element with the aperture.

Efficiency Analysis of the Organic Photoelectric Devices:

In one example, the active layer of the organic photoelectric device of the present invention uses PM6 (structure is as follows) as an electron donor and the organic semiconductor material of the present invention as an electron acceptor, wherein the structure of the organic semiconductor material DTCC-4Cl has the structure as:

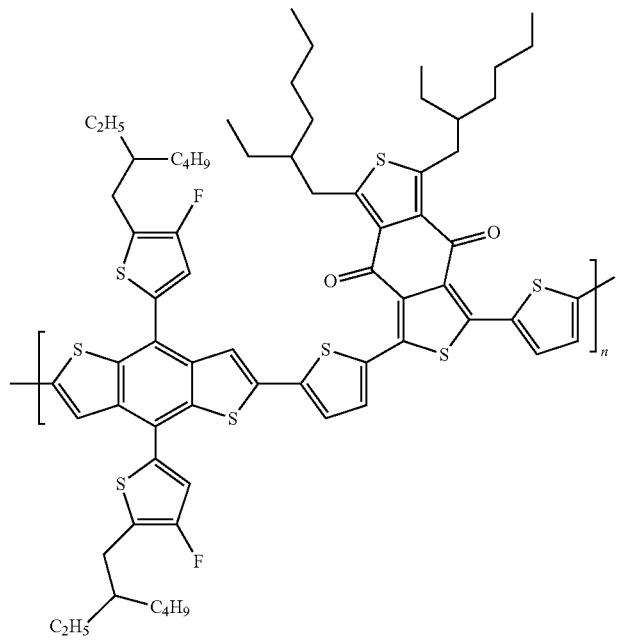

PM6

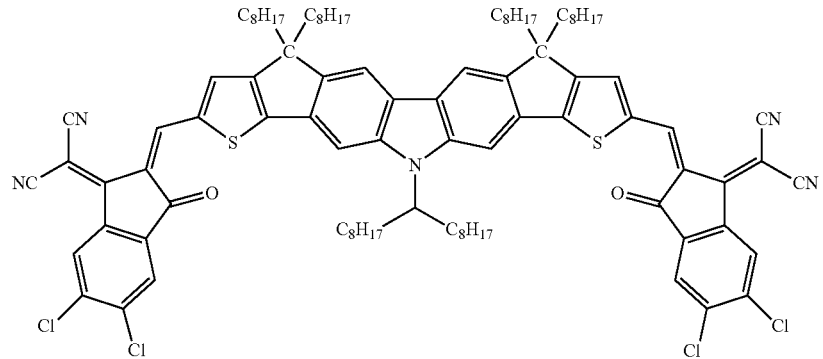

DTCC-4Cl

The active layer further includes 0.5% 1,8-diiodooctane (DIO) as an additive. In order to confirm the thermal annealing temperature and thermal annealing time required by the organic photoelectric device (PM6:DTCC-4Cl) during the manufacturing process, please refer to Table 1, which is the performance test results of the organic photoelectric device under different thermal annealing conditions. Wherein, the experiment is conducted with a ratio of PM6:DTCC-4Cl=1:1.4.

TABLE 1 organic photoelectric device (PM6:DTCC-4Cl)

| Annealing temp. (° C.) | Annealing time (min) | $V_{oc}$ (V) | $J_{sc}$ (mA/cm$^2$) | FF (%) | PCE (%) |
|---|---|---|---|---|---|
| None | None | 0.92 (0.92 ± 0.01) | 20.93 (20.88 ± 0.24) | 71.93 (70.86 ± 0.87) | 13.85 (13.39 ± 0.20) |
| 80 | 10 | 0.91 (0.91 ± 0.00) | 18.37 (18.33 ± 0.42) | 76.62 (73.98 ± 1.61) | 12.81 (12.34 ± 0.33) |
| 100 | 10 | 0.90 (0.90 ± 0.00) | 19.97 (19.52 ± 0.39) | 75.32 (75.05 ± 0.84) | 13.54 (13.19 ± 0.20) |
| 120 | 5 | 0.88 (0.88 ± 0.00) | 18.25 (18.15 ± 0.35) | 75.55 (74.06 ± 1.18) | 12.14 (11.82 ± 0.13) |
| 140 | 2 | 0.88 (0.88 ± 0.00) | 18.72 (18.47 ± 0.40) | 74.30 (73.63 ± 1.43) | 12.24 (11.96 ± 0.17) |

As shown in Table 1, this organic photoelectric device (PM6:DTCC-4Cl) under different thermal annealing conditions, we can see that the organic photoelectric device (PM6:DTCC-4Cl) made in the process of no thermal annealing, the power conversion efficiency of it is 13.85%. The performance of the organic photoelectric device (PM6:DTCC-4Cl) with the thermal annealing-free process is significantly higher than other organic photoelectric devices (PM6:DTCC-4Cl) with the thermal annealing process.

In one example, the active layer of the organic photoelectric device of the present invention uses T1 (structure is as follows) as an electron donor and the organic semiconductor material of the present invention as an electron acceptor, wherein the structure of the organic semiconductor material DTCC-4Cl.

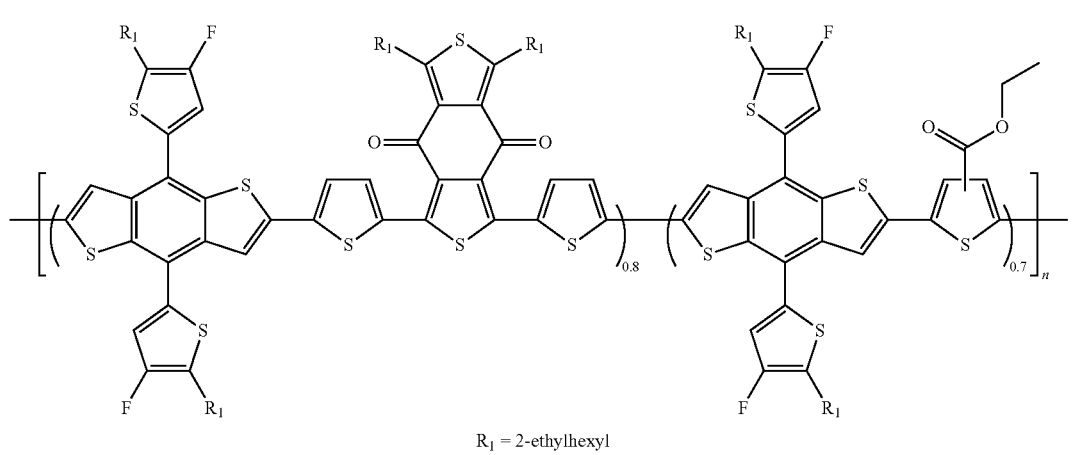

$R_1$ = 2-ethylhexyl

The active layer further includes 0.5% 1,8-diiodooctane (DIO) as an additive. Since the test results of the organic photoelectric device (PM6:DTCC-4Cl) of the previous example is that the power conversion efficiency of the thermal annealing-free process is better, the organic photoelectric device (T1:DTCC-4Cl) is also with the thermal annealing-free process. Please refer to Table 2. Table 2 shows the performance test results of the organic photoelectric device. As shown in Table 2, the power conversion efficiency (PCE) of this organic photoelectric device (T1:DTCC-4Cl) is more than 14%, which has greatly exceeded 7% of the prior art. It can be seen that the organic semiconductor material, which is an additive series of the present invention is a non-fullerene small molecule organic semiconductor material with high power conversion efficiency.

TABLE 2

| | organic photoelectric device (T1:DTCC-4Cl) | | | | |
|---|---|---|---|---|---|
| annealing | $V_{oc}$ (mV) | $J_{sc}$ (mA/cm$^2$) | $J_{calc.}^{(EQE)}$ (mA/cm$^2$) | FF (%) | PCE (%) |
| None | 0.94 (0.93 ± 0.01) | 20.03 (20.57 ± 0.66) | 18.82 | 76.26 (74.36 ± 1.82) | 14.43 (14.27 ± 0.28) |

Figure 2:
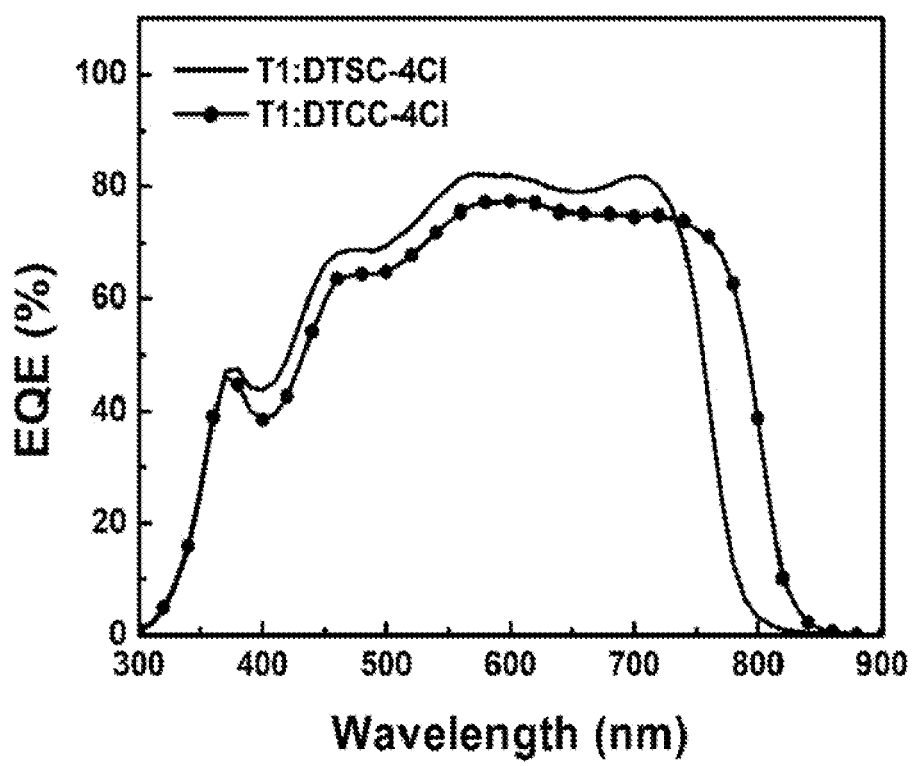
FIG. 2 shows test results of the J-V characteristics of two embodiments of the organic photoelectric devices of the present invention.
Figure 3:
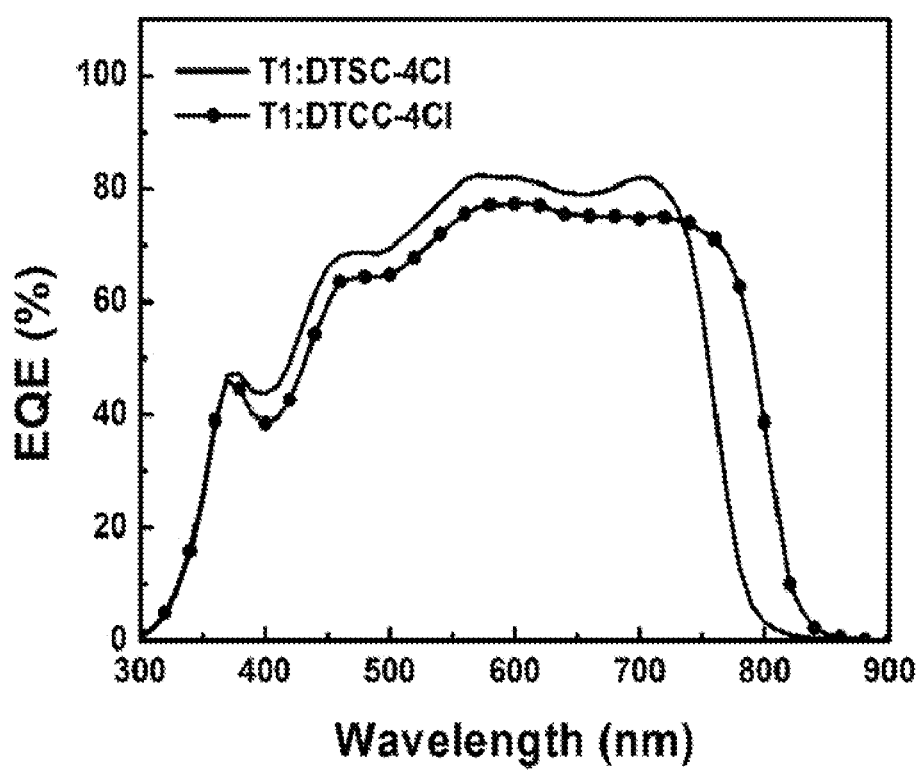
FIG. 3 shows test results of the external quantum efficiency (EQE) of two embodiments of the organic photoelectric devices of the present invention.

As shown above, the power conversion efficiency of the aforementioned organic photoelectric device (T1:DTCC-4Cl) is more than 14%. Please refer to Table 3, FIG. 2 and FIG. 3. FIG. 2 shows test results of the J-V characteristics of two embodiments of the organic photoelectric devices of the present invention, and FIG. 3 shows test results of the external quantum efficiency (EQE) of two embodiments of the organic photoelectric devices of the present invention. As shown in Table 3, FIG. 2 and FIG. 3, what is even more amazing is that when DTSC-4Cl (structure is as follows) is formed by replacing the position of C with Si which has a larger force, it can be found that the power conversion efficiency of the organic photoelectric device (DTSC-4Cl) can still reach more than 14% without additional additives. In addition, the test results of J-V characteristic and external quantum efficiency (EQE) are similar to those of the organic photovoltaic device with DTCC-4Cl with additives, which is a major breakthrough in the field.

will promote the solute accumulation and alignment to form phase separation at a specific scale. The active layer achieves the required morphology by phase separation. The morphology of the active layer is an important factor controlling the power conversion efficiency of the organic photoelectric device. When light is absorbed by the light-sensitive material, excitons are generated, which in turn diffuse to the interface between the electron donor the electron acceptor, and are separated into holes and electrons, which are transferred to the electrode end through a continuous phase in the active layer to form an electric current. Because the dissociation of excitons occurs in the interface region between the electron donor and the electron acceptor, to effectively separate the electrons and holes, to reduce the chance of recombination, and further to improve the power conversion efficiency of the organic photoelectric device, the size of the electron donor and the electron acceptor regions needs to be optimized. The size of the optimal region is

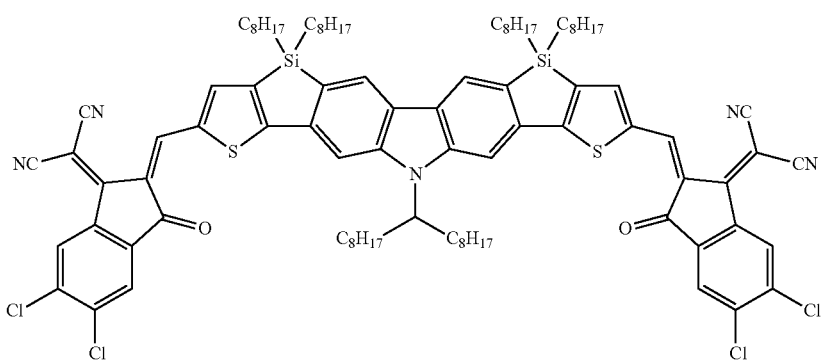

DTSC-4Cl

TABLE 3

| D:A | additive | annealing | $V_{oc}$ (mV) | $J_{sc}$ (mA/cm$^2$) | $J_{calc.}^{(EQE)}$ (mA/cm$^2$) | FF (%) | PCE (%) |
|---|---|---|---|---|---|---|---|
| T1:DTCC-4Cl | 0.5% DIO | None | 0.94 (0.93 ± 0.01) | 20.03 (20.57 ± 0.66) | 18.82 | 76.26 (74.36 ± 1.82) | 14.43 (14.27 ± 0.28) |
| T1:DTSC-4Cl | None | 120° C./5 mins | 1.00 (0.98 ± 0.01) | 19.64 (19.46 ± 0.44) | 18.18 | 73.62 (72.50 ± 1.05) | 14.46 (13.98 ± 0.25) |

In the current data theory, the effect of additives in the active layer is mainly crystallization promotion, wherein the additives must have two characteristics: (1) for at least one of the electron donor and the electron acceptor, the additive is a poor solvent; (2) the boiling point needs to be higher than the process solvent. During the coating process, a relatively large amount of additives with a high boiling point are distributed in the wet film due to the volatilization of the process solvent. Besides, the additive is a poor solvent for at least one of the electron donor and the electron acceptor which as a solute, so it will repel at least one of the electron donor and the electron acceptor. In this way, the additives related to the excitons diffusion length. The exciton diffusion length is the average distance that electrons and holes will diffuse before recombination. This length is controlled by the lifetime of the exciton and the diffusion coefficient. In organic photoelectric devices, the exciton diffusion length is generally in the range of 5 to 10 nm. If the region between the electron donor and the electron acceptor can be controlled to form this heterogeneous interface structure, the power conversion efficiency of the organic photoelectric device will be improved. It can be known that the design of the type and amount of additives will affect the morphology of the active layer, and then affect the power conversion efficiency of the organic photoelectric device.

In terms of common additives, in addition to affecting film-forming characteristics during the manufacturing process, the use of additives is unpopular in industrial production. For example, the boiling point of 1,8-diiodooctane (DIO) is still as high as 168° C. under the pressure of 6 mm-Hg. Another commonly used additive is 1-choronaphthalene (CN), and the boiling point of CN is up to 112° C. under the pressure of 5 mm-Hg. In addition, both additives are halogen-containing substances; although they are used in small amounts, they are still a major concern for waste disposal. Besides, 1,8-octanedithiol (OT), 1,8-cicholorooctane, 1,8-dibromooctane, 1,8-dicyanooctane, 1,8-octanediacetate, and 1,2-diphenoxyethane (DPE) can be used as additives, and they also have the same problems.

Compared with the prior art, in the structure of the organic semiconductor material of the present invention, and the power conversion efficiency of the organic photoelectric device with an additive series, which has a structure wherein X1 and X2 are selected from one of C and its derivatives, is more than 14%. When X1 and X2 are independently selected from one of Si, Ge and its derivatives, the power conversion efficiency of the organic photoelectric device can achieve more than 14% without adding additional additives. This is because the force of the Si atom itself is greater than the force of the C atom, which makes the intermolecular force and stacking more likely to form a highly stacked crystalline phase. Therefore, when the organic semiconductor material of the additive-free series of the present invention is combined with other organic semiconductor materials to form an active layer solution of a heterogeneous interface structure of an electron donor: an electron acceptor. Due to the strong stacking characteristics of the molecule in the active layer, the organic photoelectric device can achieve ideal phase separation characteristics without the additional additives in the manufacturing process and achieve the expected power conversion efficiency. The active layer further includes an organic solvent having solubility with not less than 5 mg/mL for the active layer.

Figure 4:
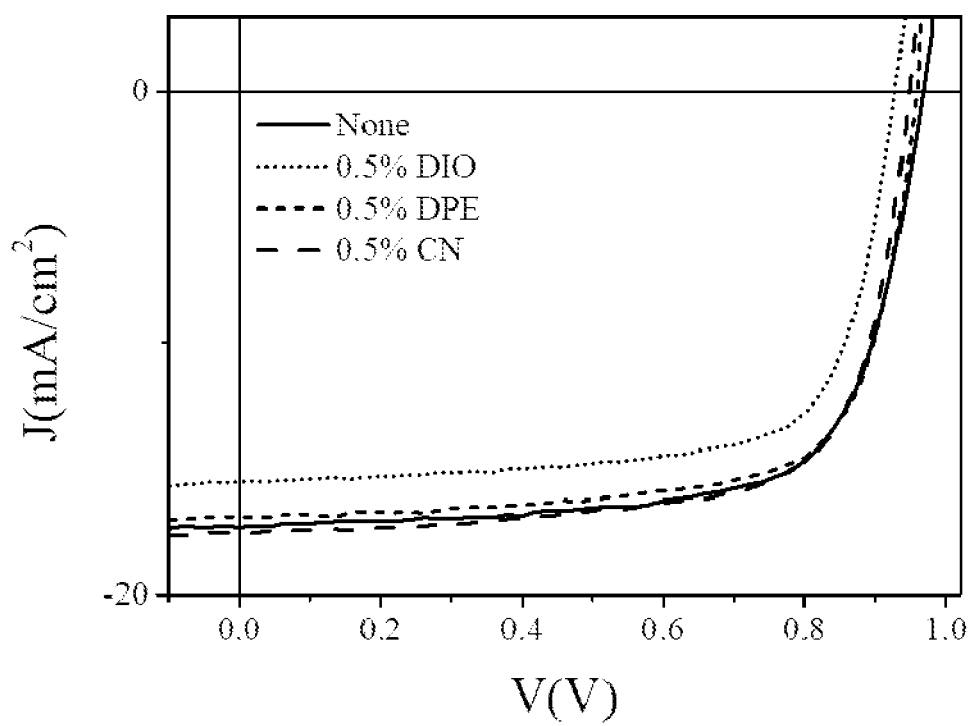
FIG. 4 shows test results of the J-V characteristics of another embodiment of the organic photoelectric device of the present invention with different additives.

Please refer to Table 4 and FIG. 4. Table 4 shows the test result of the relationship between another embodiment of the organic photoelectric device of the present invention and the additives. FIG. 4 shows test results of the J-V characteristics of another embodiment of the organic photoelectric device of the present invention with different additives. In one embodiment, the active layer of the organic photoelectric device of the present invention uses PBDB-T-F as an electron donor and the organic semiconductor material (DTSC-4F) of the present invention as an electron acceptor. The structures of these two are as follows:

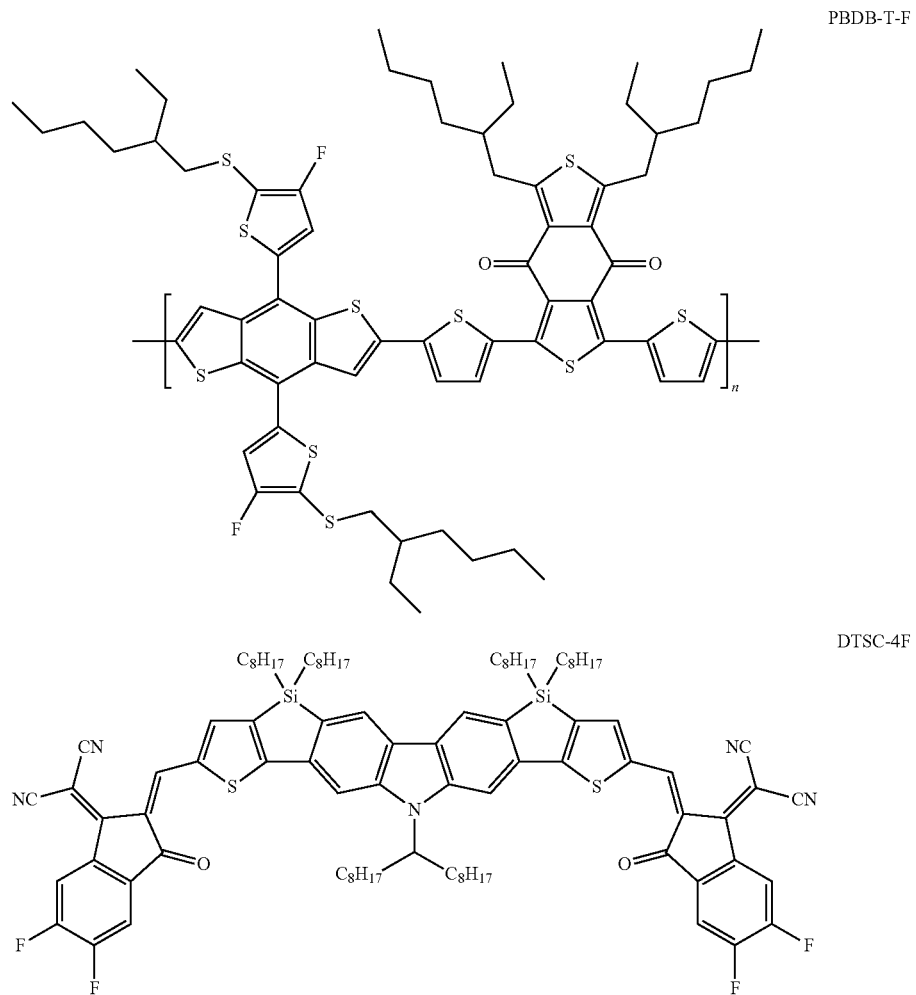

Wherein, the preparation conditions of the organic photoelectric device are ITO/ZnO/active layer/MoO$_3$ (7 nm)/Ag (150 nm). The active layer includes an electron donor: an electron acceptor at a ratio of 1:1, formulated at a concentration of 20 mg/mL with 0.3 mL of CB. The thermal annealing are 100° C. and 10 minutes. The thickness of the film is about 100 nm. The coating speed is 1750 rpm.

TABLE 4

| Additive | Added amount | $V_{oc}$ (mV) | $J_{sc}$ (mA/cm$^2$) | FF (%) | PCE (%) |
|---|---|---|---|---|---|
| organic photoelectric device (PBDB-T-F:DTSC-4F); Average (best value) | | | | | |
| None | None | 0.95(0.96) | 17.15(17.33) | 69.77(70.77) | 11.40(11.77) |
| DIO | 0.5 | 0.93(0.93) | 15.03(15.52) | 70.96(72.36) | 9.96(10.33) |
| DPE | 0.5 | 0.95(0.96) | 17.12(17.03) | 71.14(71.41) | 11.63(11.67) |
| CN | 0.1 | 0.95(0.96) | 16.91(17.04) | 69.29(70.68) | 11.10(11.56) |
|  | 0.5 | 0.95(0.94) | 17.51(17.58) | 69.72(71.08) | 11.60(11.74) |
|  | 1 | 0.94(0.94) | 17.01(17.02) | 70.72(70.90) | 11.32(11.34) |

As shown in Table 4 and FIG. 4, the power conversion efficiency of the organic photoelectric device (PBDP-T-F:DTSC-4F) without additives is much larger than that of the organic photoelectric device (PBDP-T-F:DTSC-4F) with additives of 0.5% DIO. The power conversion efficiency is approximately equal to the power conversion efficiency of an organic photoelectric device (PBDB-T-F:DTSC-4F) with additives of 0.5% DPE and 0.5% CN. In addition, according to the test results of adding different amounts of CN, it can be found that the amount of additives is non-linear relationship to the power conversion efficiency. It can be inferred that the power conversion efficiency of the organic photoelectric device (PBDB-T-F:DTSC-4F) does not tend to be significantly enhanced by the addition of additives.

Figure 5:
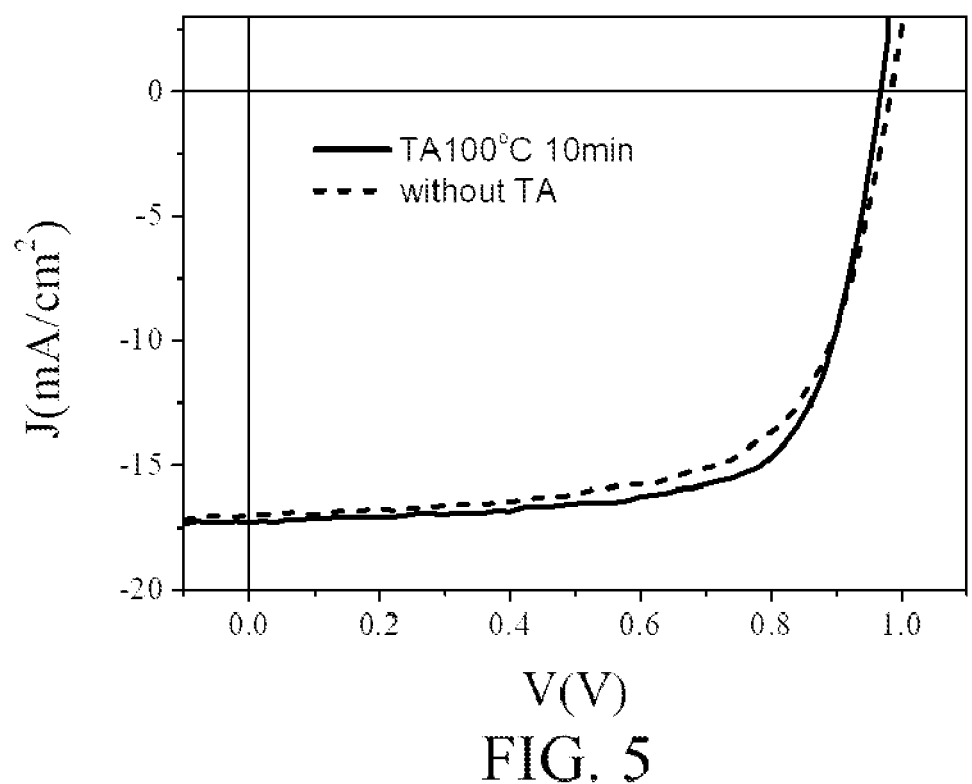
FIG. 5 shows test results of the J-V characteristics of another embodiment of the organic photoelectric device of the present invention under different thermal annealing conditions.
Figure 6:
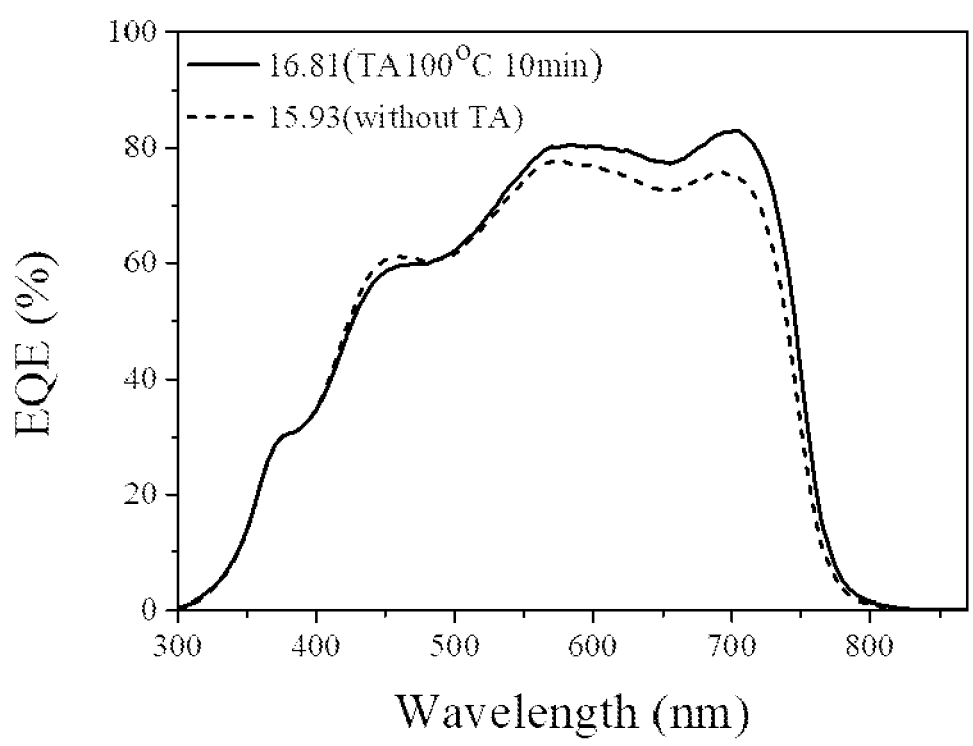
FIG. 6 shows test results of the external quantum efficiency (EQE) of another embodiment of the organic photoelectric device of the present invention under different thermal annealing conditions.

Please refer to Table 5, FIG. 5 and FIG. 6. Table 5 shows the test results of another embodiment of the organic photoelectric device of the present invention under different thermal annealing conditions. FIG. 5 shows test results of the J-V characteristics of another embodiment of the organic photoelectric device of the present invention under different thermal annealing conditions. FIG. 6 shows test results of the external quantum efficiency (EQE) of another embodiment of the organic photoelectric device of the present invention under different thermal annealing conditions. The aforementioned additive-free organic photoelectric device (PBDB-T-F:DTSC-4F) was respectively prepared by thermal annealing and under thermal annealing conditions of 100° C. and 10 minutes.

TABLE 5

| Annealing condition | $V_{oc}$ (mV) | $J_{sc}$ (mA/cm$^2$) | FF (%) | PCE (%) |
|---|---|---|---|---|
| organic photoelectric device (PBDB-T-F:DTSC-4F); Average (best value) | | | | |
| None | 0.97(0.98) | 16.78(17.02) | 66.06(65.59) | 10.79(10.94) |
| 100° C./10 min | 0.93(0.93) | 15.03(15.52) | 69.77(70.77) | 11.40(11.77) |

As shown in Table 5, FIG. 5 and FIG. 6, when the additive-free organic photoelectric device (PBDB-T-F: DTSC-4F) are prepared under different thermal annealing conditions, the power conversion efficiency of them are more than 10%.

Figure 7:
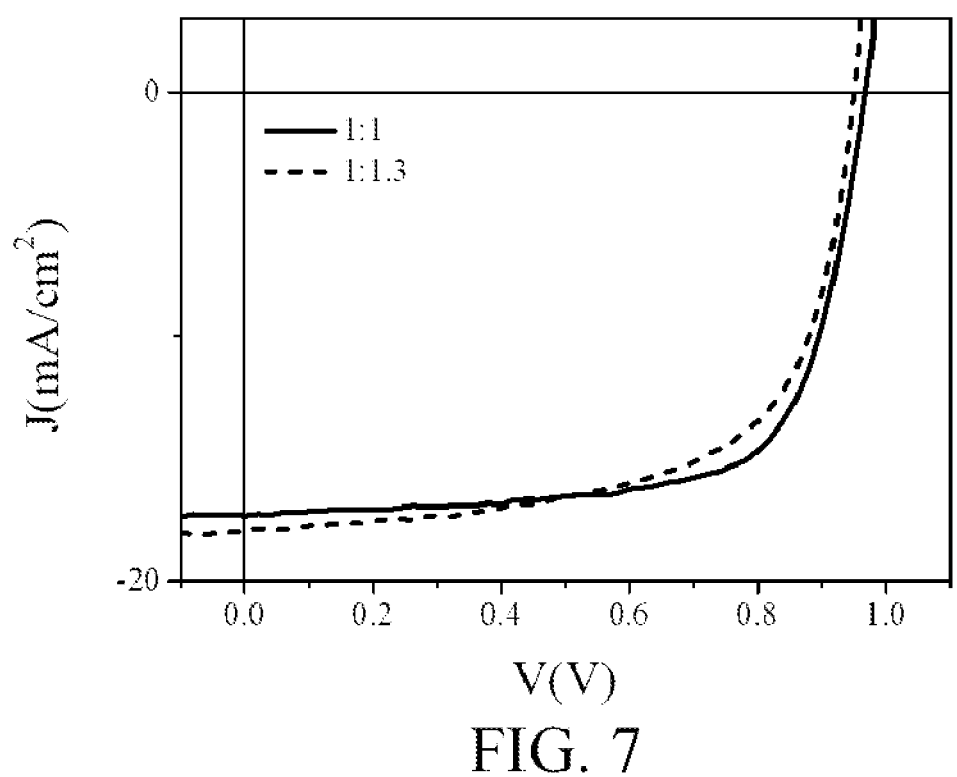
FIG. 7 shows test results of the J-V characteristics of another embodiment of the organic photoelectric device of the present invention at different configuration ratios.
Figure 8:
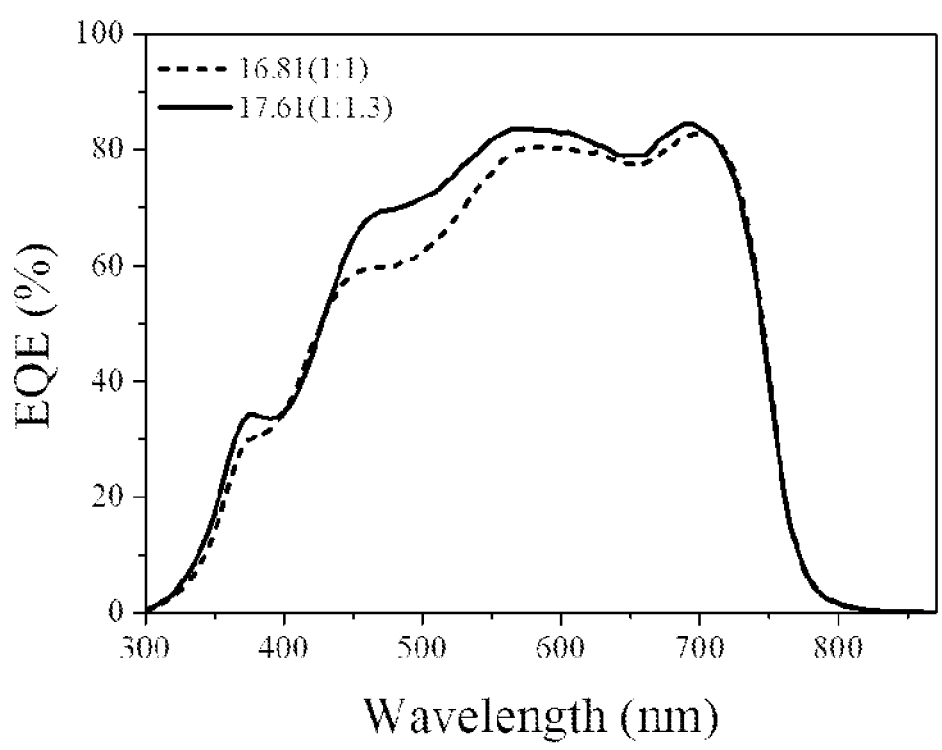
FIG. 8 shows test results of the external quantum efficiency (EQE) of another embodiment of the organic photoelectric device of the present invention at different configuration ratios.

Please refer to Table 6, FIG. 7 and FIG. 8. Table 6 shows the test results of another embodiment of the organic photoelectric device of the present invention at different configuration ratios. FIG. 7 shows test results of the J-V characteristics of another embodiment of the organic photoelectric device of the present invention at different configuration ratios. FIG. 8 shows test results of the external quantum efficiency (EQE) of another embodiment of the organic photoelectric device of the present invention at different configuration ratios. The aforementioned organic additive-free organic photoelectric devices (PBDB-T-F:DTSC-4F) are respectively arranged at an electron donor (D):electron acceptor (A) ratio of 1:1 and 1:1.3.

TABLE 6

| D:A | $V_{oc}$ (mV) | $J_{sc}$ (mA/cm$^2$) | FF (%) | PCE (%) |
|---|---|---|---|---|
| organic photoelectric device (PBDB-T-F:DTSC-4F); Average (best value) | | | | |
| 1:1 | 0.95(0.96) | 17.15(17.33) | 69.77(70.77) | 11.40(11.77) |
| 1:1.3 | 0.94(0.96) | 17.96(17.95) | 63.42(63.09) | 10.82(10.87) |

As shown in Table 6, FIG. 7 and FIG. 8, when the additive-free series organic photoelectric devices (PBDB-T-F:DTSC-4F) are configured at different ratios, the power conversion efficiency of them are more than 10%.

Please refer to Table 7. Table 7 shows the test results of another embodiment of the organic photoelectric device of the present invention with different electron donors. The aforementioned additive-free series organic photoelectric devices (DTSC-4F) are respectively arranged with different electron donors at a ratio of 1:1. The structures of D1 and D2 are as follows:

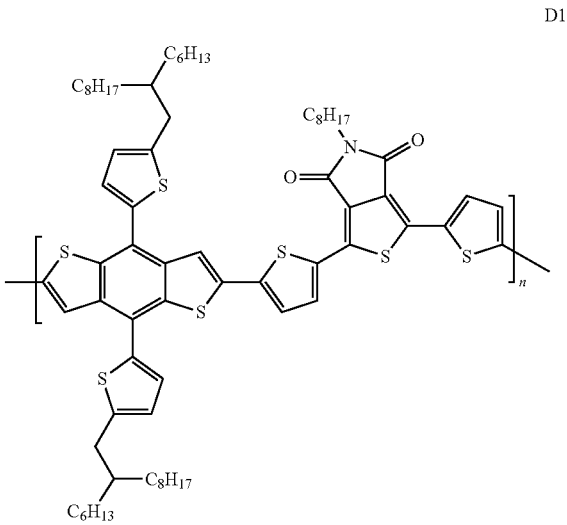

D1

-continued

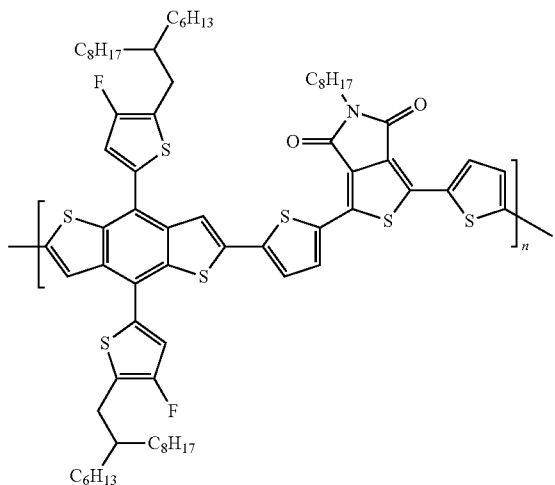

D2

TABLE 7

| organic photoelectric device (DTSC-4F); | | | | |
|---|---|---|---|---|
| Electron donor | $V_{oc}$ (V) | $J_{sc}$ (mA/cm$^2$) | FF (%) | PCE (%) |
| D1 | 0.96 | 16.0 | 72.2 | 11.1 |
| D2 | 1.01 | 16.1 | 68.3 | 11.1 |

As shown in Table 7, when the additive-free series organic photoelectric devices (DTSC-4F) are respectively used with different electron donors, the power conversion efficiency of them are more than 10%.

In summary, the power conversion efficiency of the additive-free series organic photoelectric device of the present invention is more than 10% under different conditions such as the amount of additives added, the configuration ratio, the thermal annealing condition and the type of the electron donor. This means that the additive-free series organic photoelectric device of the present invention has good stability.

With the detailed description of the above embodiments, it is hoped that the features and spirit of the present invention can be more clearly described, and the scoped of the present invention is not limited by the embodiments disclosed above. On the contrary, the intention is to cover various changes and equivalent arrangements within the scope of the patents to be applied for in the present invention.

What is claimed is:

1. An organic semiconductor material, comprising an electron acceptor and an electron donor, the electron acceptor comprising a structure of Formula I:

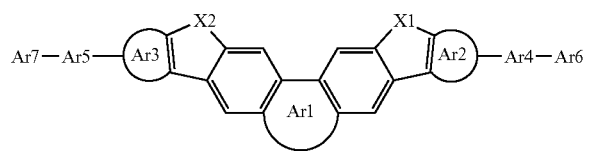

(Formula I)

wherein X1 and X2 can be the same or different, and X1 and X2 are independently selected from one of the following: C, Si, Ge and derivatives thereof;

Ar1 is selected from the group consisting of five-member heterocyclic ring with and without substitutions, and six-member heterocyclic ring with and without substitutions;

Ar2 and Ar3 can be the same or different, and Ar2 and Ar3 are independently selected from the group consisting of aromatic ring with and without substitutions, heterocyclic ring with and without substitutions, fused ring with and without substitutions and fused heterocyclic ring with and without substitutions, wherein Ar2 and Ar3 include at least one of five-member ring and six-member ring, and the number of the five-member ring and the six-member ring in Ar2 is selected from a range from 1 to 3, and the number of the five-member ring and the six-member ring in Ar3 is selected from a range from 1 to 3;

Ar4 and Ar5 can be the same or different, and Ar4 and Ar5 are independently selected from the group consisting of aromatic ring with and without substitutions, heterocyclic ring with and without substitutions, fused ring with and without substitutions and fused heterocyclic ring with and without substitutions, wherein Ar4 and Ar5 include at least one of five-member ring and six-member ring, and the number of the five-member ring and the six-member ring in Ar4 is selected from a range from 0 to 3, and the number of the five-member ring and the six-member ring in Ar5 is selected from a range from 0 to 3;

Ar6 and Ar7 can be the same or different, and Ar6 and Ar7 are independently selected from the group consisting of electron-withdrawing aromatic ring with and without substitutions, electron-withdrawing heterocyclic ring with and without substitutions, electron-withdrawing fused ring with and without substitutions and electron-withdrawing fused heterocyclic ring with and without substitutions;

Ar6 bonds to Ar2 or Ar4 with single bond or double bond; and

Ar7 bonds to Ar3 or Ar5 with single bond or double bond; and the electron donor being one selected from the following polymers:

PM6
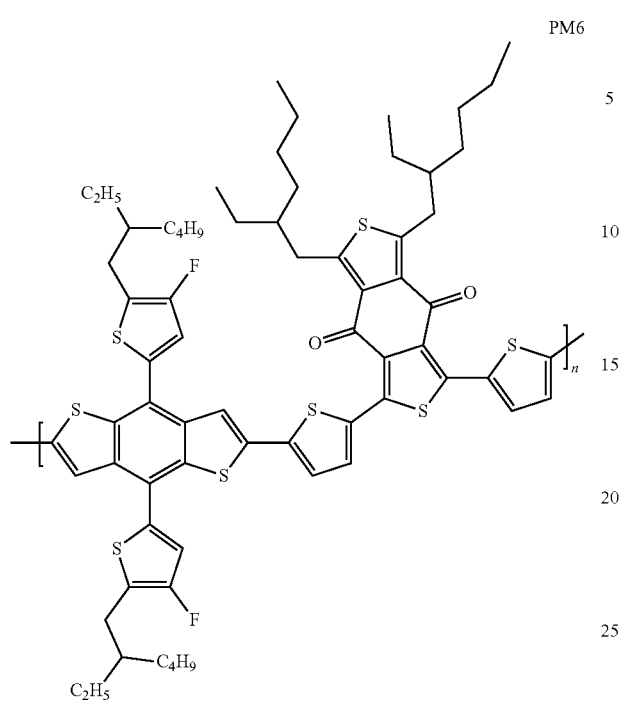
PBDB-T-F
T1
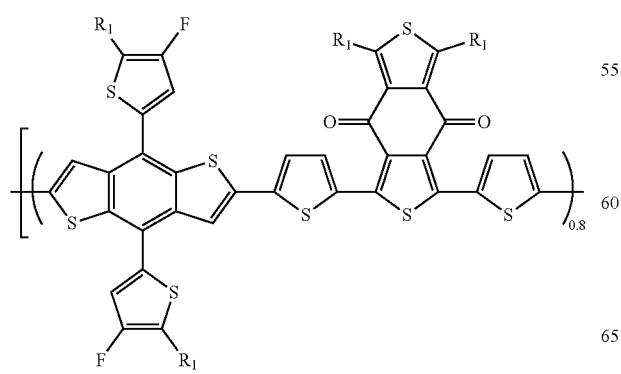
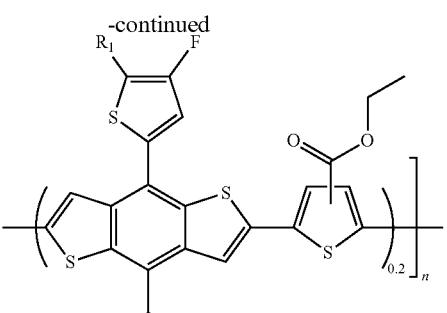
$R_1$ = 2-ethylhexyl
D1
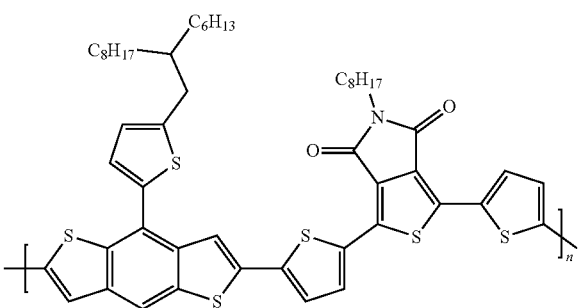
D2
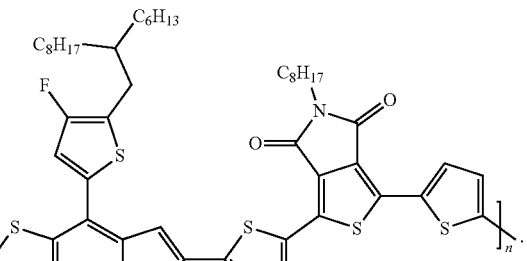
2. The organic semiconductor material of the claim 1, wherein the substitution of Ar1, Ar2, Ar3, Ar4, Ar5, Ar6, and Ar7 is selected from the group consisting of: C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

3. The organic semiconductor material of the claim 1, wherein Ar1 comprising a structure of formula II:

(Formula II)

wherein, X3 is selected from one of following: C, S, Se, Te, NR1, CR1$_2$ and SiR1$_2$, and R1 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

4. The organic semiconductor material of the claim 1, wherein Ar2 and Ar3 are independently selected from the following structure:

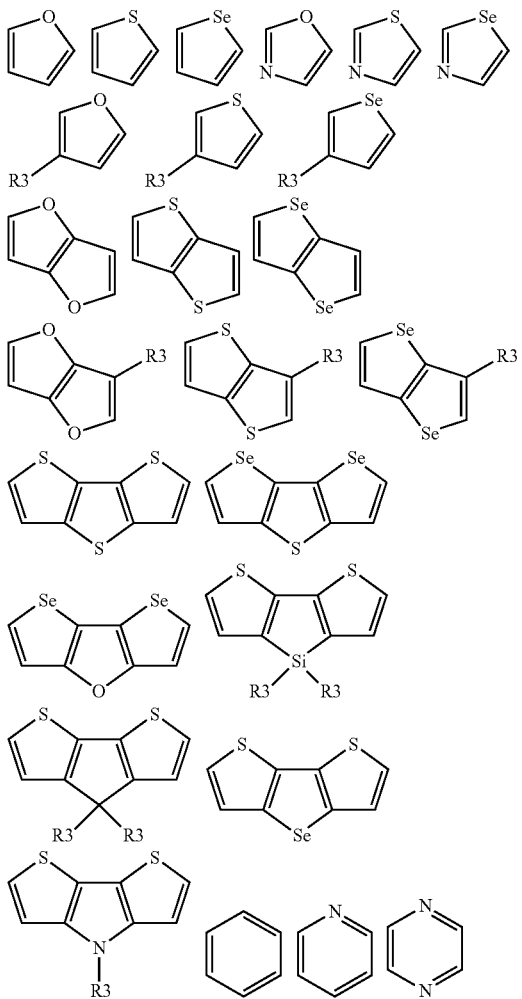

-continued

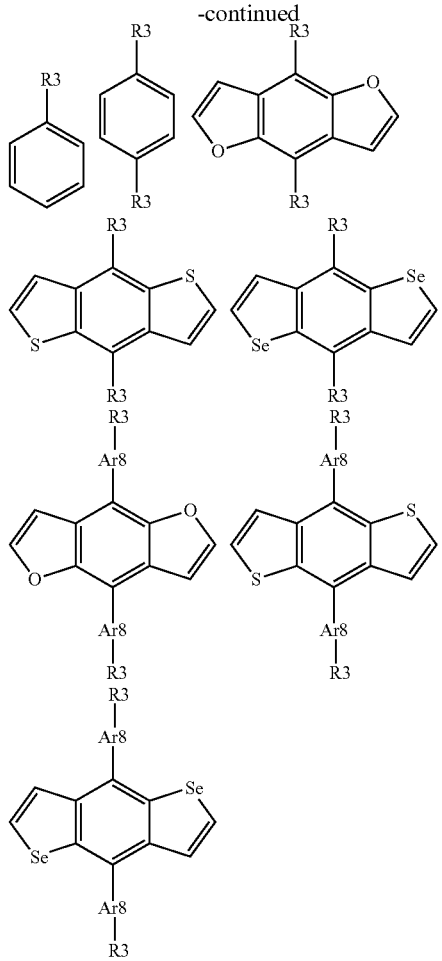

wherein, R3 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen; and Ar8 is selected from the group consisting of aromatic ring with and without substitutions, heterocyclic ring with and without substitutions, fused ring with and without substitutions and fused heterocyclic ring with and without substitutions.

5. The organic semiconductor material of the claim 1, wherein Ar4 and Ar5 are independently selected from the following structure:

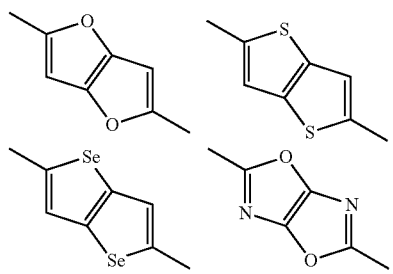

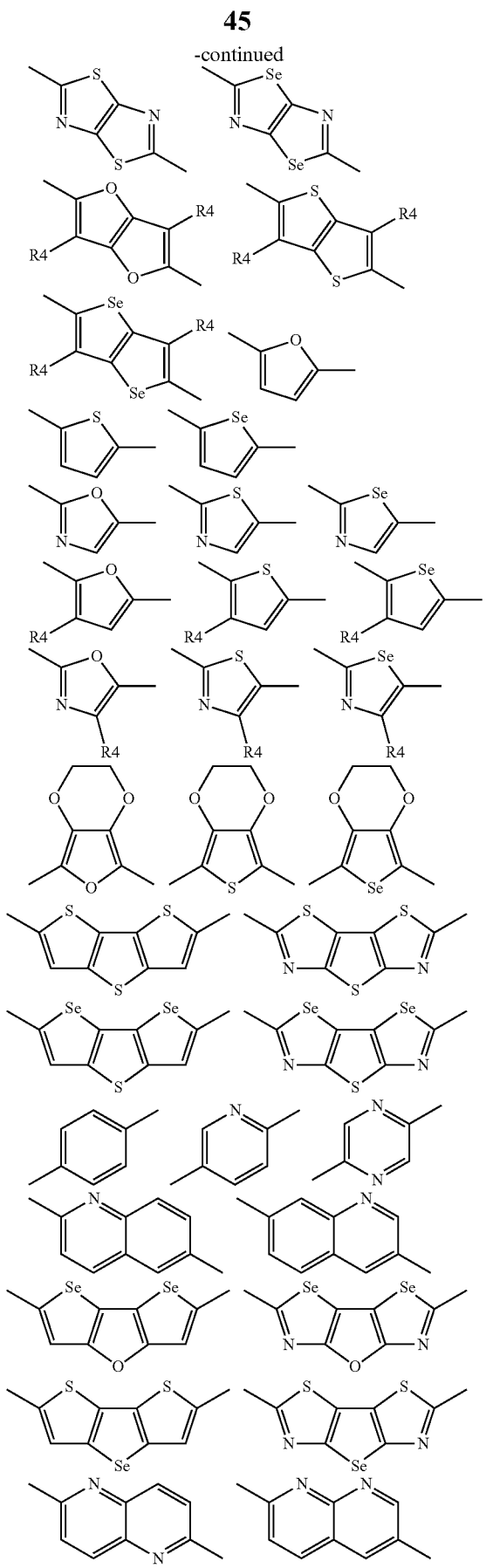
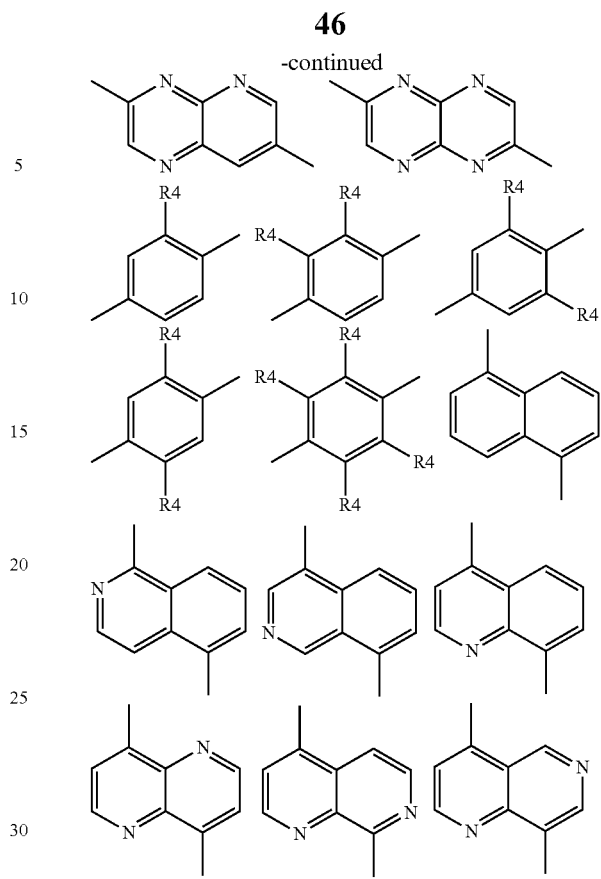

wherein, R4 is selected from the group consisting of C1-C30 alkyl, C1-C30 branched alkyl, C1-C30 silyl, C1-C30 ester, C1-C30 alkoxy, C1-C30 alkylthio, C1-C30 haloalkyl, C1-C30 olefin, C1-C30 alkyne, C1-C30 cyano-containing carbon chain, C1-C30 nitro-containing carbon chain, C1-C30 hydroxy-containing carbon chain, C1-C30 keto-containing carbon chain, oxygen and halogen.

6. The organic semiconductor material of the claim 1, wherein Ar6 and Ar7 are independently selected from the following structure:

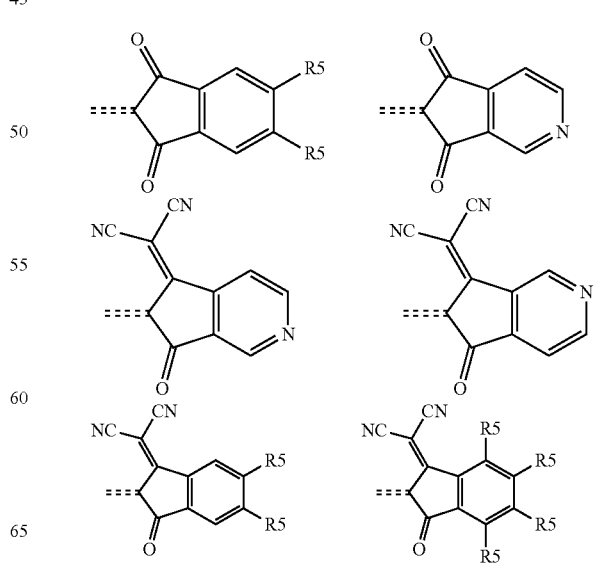

-continued

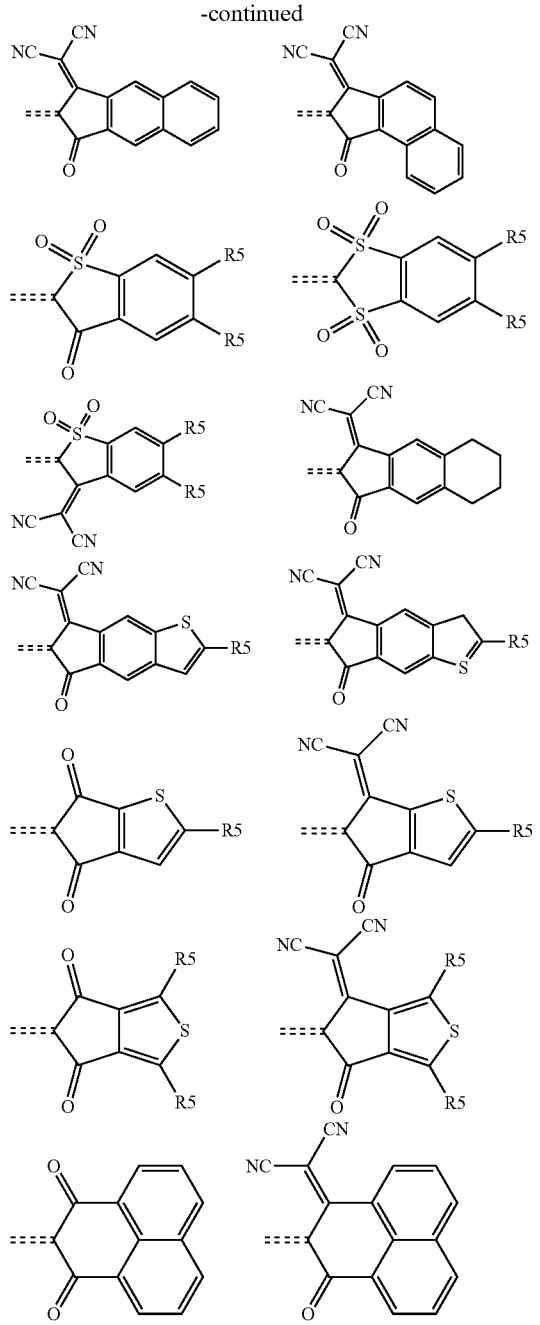
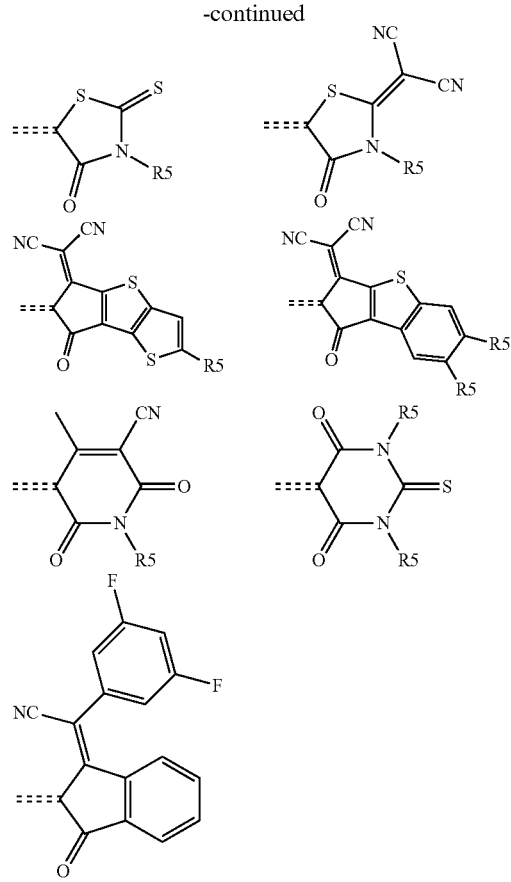

wherein, R5 is selected from the group consisting of C1-C20 alkyl, C1-C20 alkoxy, C1-C20 carbonyl, C1-C20 ester, cyano, oxygen, hydrogen, and halogen.

7. An organic photoelectric device comprising:
a first electrode including a transparent electrode;
a first carrier transfer layer;
an active layer which at least comprises the organic semiconductor material of the claim 1;
a second carrier transfer layer; and
a second electrode;
wherein the second carrier transfer layer is disposed between the active layer and the second electrode.

* * * * *